(12) United States Patent
Yamaguchi

(10) Patent No.: US 11,774,772 B2
(45) Date of Patent: Oct. 3, 2023

(54) MEDICAL IMAGE PROCESSING DEVICE, MEDICAL OBSERVATION SYSTEM, AND IMAGE PROCESSING METHOD

(71) Applicant: Sony Olympus Medical Solutions Inc., Tokyo (JP)

(72) Inventor: Kazuhiro Yamaguchi, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 339 days.

(21) Appl. No.: 17/167,110

(22) Filed: Feb. 4, 2021

(65) Prior Publication Data
US 2021/0294084 A1    Sep. 23, 2021

(30) Foreign Application Priority Data
Mar. 19, 2020 (JP) .................. 2020-049175

(51) Int. Cl.
| G02B 21/00 | (2006.01) |
| G02B 27/14 | (2006.01) |
| G02B 21/36 | (2006.01) |
| A61B 1/00 | (2006.01) |

(52) U.S. Cl.
CPC ...... *G02B 27/141* (2013.01); *A61B 1/000095* (2022.02); *G02B 21/0012* (2013.01); *G02B 21/0032* (2013.01); *G02B 21/0076* (2013.01); *G02B 21/361* (2013.01)

(58) Field of Classification Search
CPC .............. G02B 27/141; G02B 21/0012; G02B 21/0032; G02B 21/0076; G02B 21/361; G02B 23/2484; G02B 27/1013; A61B 1/000095; A61B 1/00186; A61B 1/042; A61B 1/043; A61B 1/0638
See application file for complete search history.

(56) References Cited

U.S. PATENT DOCUMENTS

| 2018/0082411 A1* | 3/2018 | Sato ................... G01N 21/6456 |
| 2018/0116520 A1* | 5/2018 | Yamamoto ......... A61B 1/00096 |
| 2018/0153386 A1* | 6/2018 | Omori .................. A61B 1/0005 |
| 2020/0252554 A1* | 8/2020 | Themelis ............. H04N 5/2621 |

* cited by examiner

*Primary Examiner* — Mustak Choudhury
(74) *Attorney, Agent, or Firm* — XSENSUS LLP

(57) ABSTRACT

A medical image processing device includes an image processing unit configured to perform image processing, based on image data generated by imaging reflected light of first visible light emitted to an object and fluorescence when a light source device simultaneously emits the first visible light and excitation light that excites a fluorescent substance to emit the fluorescence. The image processing unit is configured to generate an interpolation pixel value corresponding to a component of second visible light in a wavelength band different from a wavelength band of the first visible light, based on a first pixel value and output from a pixel receiving the reflected light of the first visible light emitted to the object, generate a background image based on the first pixel value and the interpolation pixel value, and generate a fluorescence image based on a second pixel value included in the image data and output from a pixel receiving the fluorescence.

18 Claims, 14 Drawing Sheets

| $P_{11}$ | $P_{12}$ | $P_{13}$ | $P_{14}$ | ... |
| $P_{21}$ | $P_{22}$ | $P_{23}$ | $P_{24}$ | ... |
| $P_{31}$ | $P_{32}$ | $P_{33}$ | $P_{34}$ | ... |
| $P_{41}$ | $P_{42}$ | $P_{43}$ | $P_{44}$ | ... |

| $R_{11}$ | $Gr_{12}$ | $R_{13}$ | $Gr_{14}$ | ... |
| $Gb_{21}$ | $B_{22}$ | $Gb_{23}$ | $B_{24}$ | ... |
| $R_{31}$ | $Gr_{32}$ | $R_{33}$ | $Gr_{34}$ | ... |
| $Gb_{41}$ | $B_{42}$ | $Gb_{43}$ | $B_{44}$ | ... |

R, G CORRELATION 0.814337

R, B CORRELATION 0.824038

B, G CORRELATION 0.969068

R, G CORRELATION 0.662769

R, B CORRELATION 0.698361

B, G CORRELATION 0.958993

FIG.10

| | R-G CORRELATION | R-B CORRELATION | G-B CORRELATION |
|---|---|---|---|
| IMAGE 1 | 0.240987 | 0.307373 | 0.914499 |
| IMAGE 2 | 0.800874 | 0.616988 | 0.927488 |
| IMAGE 3 | 0.736272 | 0.704615 | 0.962935 |
| IMAGE 4 | 0.662769 | 0.698361 | 0.958993 |
| IMAGE 5 | 0.800874 | 0.616988 | 0.927488 |
| IMAGE 6 | 0.814337 | 0.824038 | 0.969068 |
| AVERAGE | 0.676019 | 0.62806 | 0.943412 |

MEDICAL IMAGE PROCESSING DEVICE, MEDICAL OBSERVATION SYSTEM, AND IMAGE PROCESSING METHOD

CROSS-REFERENCE TO RELATED APPLICATION

This application claims priority from Japanese Application No. 2020-049175, filed on Mar. 19, 2020, the contents of which are incorporated by reference herein in its entirety.

BACKGROUND

The present disclosure relates to a medical image processing device, a medical observation system, and an image processing method.

In surgical microscopes, there is known a technique in which red light, green light, and blue light are guided to three image sensors via a dichroic beam splitter, and infrared light is guided to one of the three image sensors to observe a fluorescence image and a visible light image (see, e.g., JP 5646844 B2).

SUMMARY

In JP 5646844 B2 described above, the fluorescence image and the visible light image are observed using three image sensors, and thus, there is a problem that reduction in size of the device is made difficult.

There is a need for a medical image processing device, a medical observation system, and an image processing method that are able to reduce a size of a device.

According to one aspect of the present disclosure, there is provided a medical image processing device including an image processing unit configured to perform image processing, based on image data generated by imaging reflected light of first visible light emitted to an object and fluorescence, by a medical imaging device, when a light source device simultaneously emits, to the object, the first visible light and excitation light that excites a fluorescent substance to emit the fluorescence, wherein the image processing unit is configured to generate an interpolation pixel value corresponding to a component of second visible light in a band different from that of the first visible light, based on a first pixel value included in the image data and output from a pixel receiving the reflected light of the first visible light emitted to the object, generate a background image based on the first pixel value and the interpolation pixel value, and generate a fluorescence image based on a second pixel value included in the image data and output from a pixel receiving the fluorescence.

BRIEF DESCRIPTION OF THE DRAWINGS

FIG. 3 is a diagram schematically illustrating a configuration of a pixel portion according to the first embodiment;

FIG. 4 is a diagram schematically illustrating a configuration of a color filter according to the first embodiment;

FIG. 10 is a table illustrating a correlation between pixels located at the same positions of red images, green images, and blue images that are obtained by separating a plurality of medical images of a surgical site (biological tissue) of a subject;

DETAILED DESCRIPTION

Figure 1:
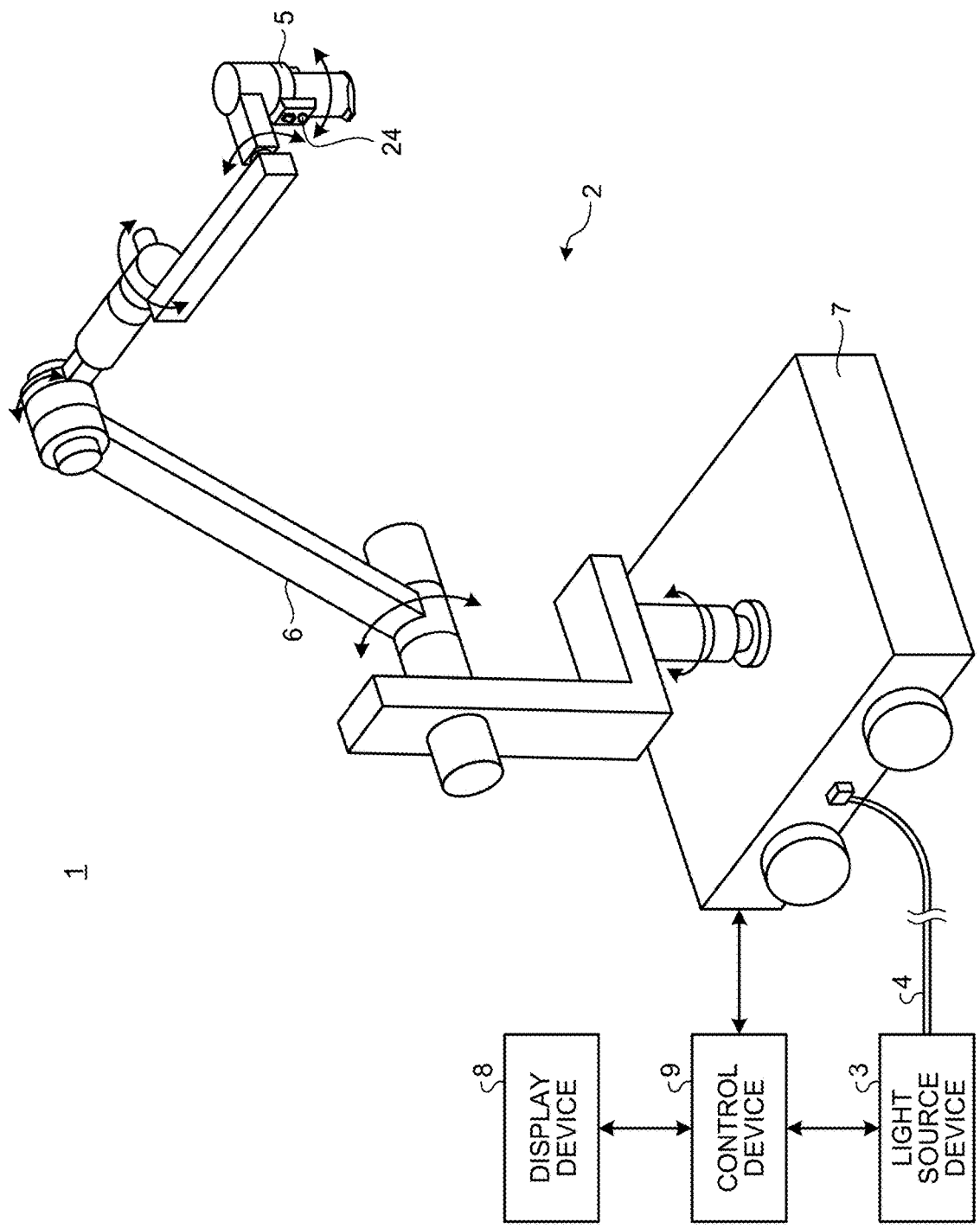
FIG. 1 is a diagram illustrating the overall configuration of a medical observation system according to a first embodiment.

Modes for carrying out the present disclosure (hereinafter, referred to as "embodiments") will be described below in detail with reference to the drawings. Note that the present disclosure is not limited to the following embodiments. In addition, the drawings referred to in the following descriptions are merely schematically illustrated in shape, size, and positional relationship so as to understand the contents of the present disclosure. In other words, the present disclosure is not limited only to the shapes, sizes, and positional relationships exemplified in the drawings.

First Embodiment

Schematic Configuration of Medical Observation System
FIG. 1 is a diagram illustrating the overall configuration of a medical observation system according to a first embodiment. A medical observation system 1 illustrated in FIG. 1 includes a medical observation device 2, a light source device 3, a display device 8, and a control device 9, the medical observation device 2 being configured to function as a microscope to magnify a minute portion of an object to be observed, for observation, the light source device 3 being configured to supply illumination light to the observation device 2 via a light guide 4 including optical fiber or the like, the display device 8 being configured to display an image based on image data captured by the observation device 2, the control device 9 being configured to integrally control the operation of the medical observation system 1.

Schematic Configuration of Observation Device
First, a schematic configuration of the observation device 2 will be described. The observation device 2 includes a microscope unit 5, a support unit 6, and a base portion 7. The microscope unit 5 is configured to observe a minute portion of an object to be observed, the support unit 6 is connected to a base end portion of the microscope unit 5 and configured to rotatably support the microscope unit 5, and the base portion 7 is configured to rotatably hold a base end portion of the support unit 6 and to be movable on a floor surface.

The microscope unit 5 has a columnar appearance and internally includes an optical system, an image sensor (not illustrated), and a light emitting unit (not illustrated), the optical system having a zoom and a focus function, the image sensor being configured to receive light focused into an image of an object by the optical system, perform photoelectric conversion, and generate image data, the light emitting unit being configured to emit illumination light to an object to be observed. Furthermore, the microscope unit 5 has a side surface on which various switches are provided, the various switches constituting an input unit 24 receiving input of operation instruction for the observation device 2. The microscope unit 5 has an opening surface at a lower end and the opening surface is provided with a cover glass (not illustrated) that protects the optical system and the like positioned therein. A user such as an operator is allowed to move the microscope unit 5, change the angle of the microscope unit 5, change the modes of the observation device 2, or perform zoom or focus operation, while operating the various switches with the microscope unit 5 held. The shape of the microscope unit 5 is not limited to the cylindrical shape but may be, for example, a polygonal cylindrical shape.

Under the control by the control device 9, the light source device 3 supplies, to the observation device 2 via the light guide 4, illumination light of at least one of infrared light and white light including light in a red wavelength band, light in a green wavelength band, and light in a blue wavelength band. The light source device 3 includes a discharge lamp such as a xenon lamp or metal halide lamp, a solid-state light emitting device such as a light emitting diode (LED) or a laser diode (LD), or a light emitting member such as a halogen lamp.

The display device 8 displays an image to be displayed that is generated by the control device 9 or various information about the medical observation system. The display device 8 includes liquid crystal, organic electro luminescence (EL), or the like. The display device 8 displays a 2D image or 3D image.

The control device 9 integrally controls the respective units of the medical observation system 1. The control device 9 is achieved by using a memory and a general-purpose processor such as a central processing unit (CPU) or a processor including hardware such as various arithmetic circuits performing specific functions, such as an application specific integrated circuit (ASIC) or graphics processing unit (GPU). Furthermore, the control device 9 may include a field programmable gate array (FPGA: not illustrated) that is a kind of programmable integrated circuit. Note that when the FPGA is included, a memory for storing configuration data may be provided so that the FPGA as the programmable integrated circuit is configured based on the configuration data read from the memory. The configuration of the control device 9 will be described in detail later.

Figure 2:
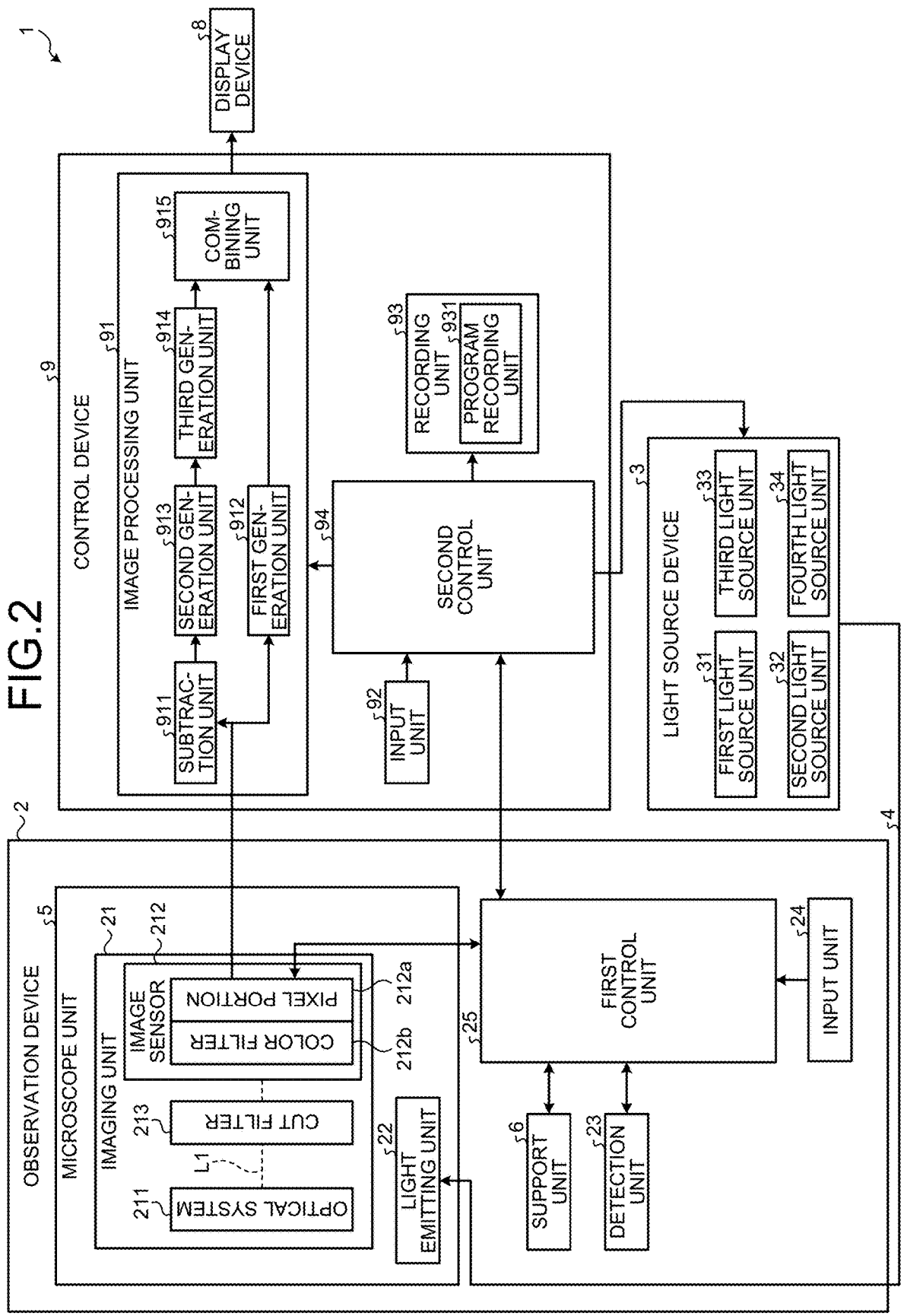
FIG. 2 is a block diagram illustrating a functional configuration of the medical observation system according to the first embodiment.

Functional Configuration of Medical Observation System
Next, the functional configuration of the medical observation system 1 will be described. FIG. 2 is a block diagram illustrating the functional configuration of the medical observation system 1.

Functional Configuration of Observation Device
First, the functional configuration of the observation device 2 will be described.

The observation device 2 includes the microscope unit 5, a detection unit 23, the input unit 24, and a first control unit 25.

The microscope unit 5 includes an imaging unit 21 and a light emitting unit 22, the imaging unit 21 being configured to generate image data by magnifying an image of the object to be observed that is an observation target, the light emitting unit 22 being configured to irradiate the object to be observed with illumination light supplied from the light source device 3.

The imaging unit 21 includes an optical system 211, an image sensor 212, and a cut filter 213. Note that the imaging unit 21 functions as a medical imaging device according to the first embodiment.

The optical system 211 has a zoom and a focus function and forms an image of the object on a light receiving surface of the image sensor 212 via the cut filter 213. The optical system 211 is achieved by using one or a plurality of lenses, a motor configured to move the lenses along an optical path L1, and the like.

The image sensor 212 receives light focused into an image of an object by the optical system 211 via the cut filter 213, performs photoelectric conversion, and generates image data (RAW data). The image sensor 212 is achieved by using an image sensor, such as a charge coupled device (CCD) or complementary metal oxide semiconductor (CMOS). The image sensor 212 includes a pixel portion 212a and a color filter 212b.

FIG. 3 is a diagram schematically illustrating a configuration of the pixel portion 212a. As illustrated in FIG. 3, in the pixel portion 212a, a plurality of pixels $P_{n,m}$ (n=an integer of 1 or more, m=an integer of 1 or more), such as photodiodes, accumulating electric charge according to an amount of light is arranged in a two-dimensional matrix. Under the control by the first control unit 25, the pixel portion 212a reads an image signal as image data from a pixel $P_{n,m}$ in a read area set as a read target, of the plurality of pixels $P_{n,m}$, and outputs the image data to the control device 9. Specifically, the image data generated by the pixel portion 212a is transmitted to the control device 9 via a transmission cable. Note that the image data generated by the pixel portion 212a may be subjected to E/O conversion so as to be transmitted to the control device 9 by an optical signal.

FIG. 4 is a diagram schematically illustrating a configuration of the color filter 212b. The color filter 212b illustrated in FIG. 4 includes a Bayer array having 2×2 filters as one unit. The color filter 212b includes a filter R configured to transmit light in a red wavelength band, two filters G (filter Gr, filter Gb) configured to transmit light in a green wavelength band, and a filter B configured to transmit light in a blue wavelength band.

In the following description, a pixel $P_{n,m}$ having a light receiving surface on which the filter R is arranged is referred to as an R pixel, a pixel $P_{n,m+1}$ having a light receiving surface on which the filter Gr is arranged is referred to as a Gr pixel, a pixel $P_{n,m+1}$ having a light receiving surface on which the filter Gb is arranged is referred to as a Gb pixel (hereinafter, the Gr pixel and the Gb pixel are collectively referred to as a G pixel), and pixels $P_{n+1,m+1}$ having a light receiving surface on which the filter B is arranged is referred to as a B pixel. Furthermore, in the first embodiment, the filter R functions as a first filter configured to transmit light (first visible light) in a red wavelength band and fluorescence, the filter B functions as a second filter configured to transmit light (second visible light) in a blue wavelength band and fluorescence, and the filter G functions as a third filter configured to transmit light (third visible light) in a green wavelength band and fluorescence. In other words, a pixel value of the R pixel includes components of reflected red light and fluorescence, a pixel value of the G pixel (Gr pixel, Gb pixel) includes components of reflected green light and fluorescence, and a pixel value of the B pixel includes components of reflected blue light and fluorescence.

The cut filter 213 is arranged on the optical path L1 between the optical system 211 and the image sensor 212. The cut filter 213 blocks light having a wavelength component (e.g., 740±10 nm) of excitation light included in an image of the object formed by the optical system 211 and transmits light having a wavelength component of light other than the excitation light.

Figure 5:
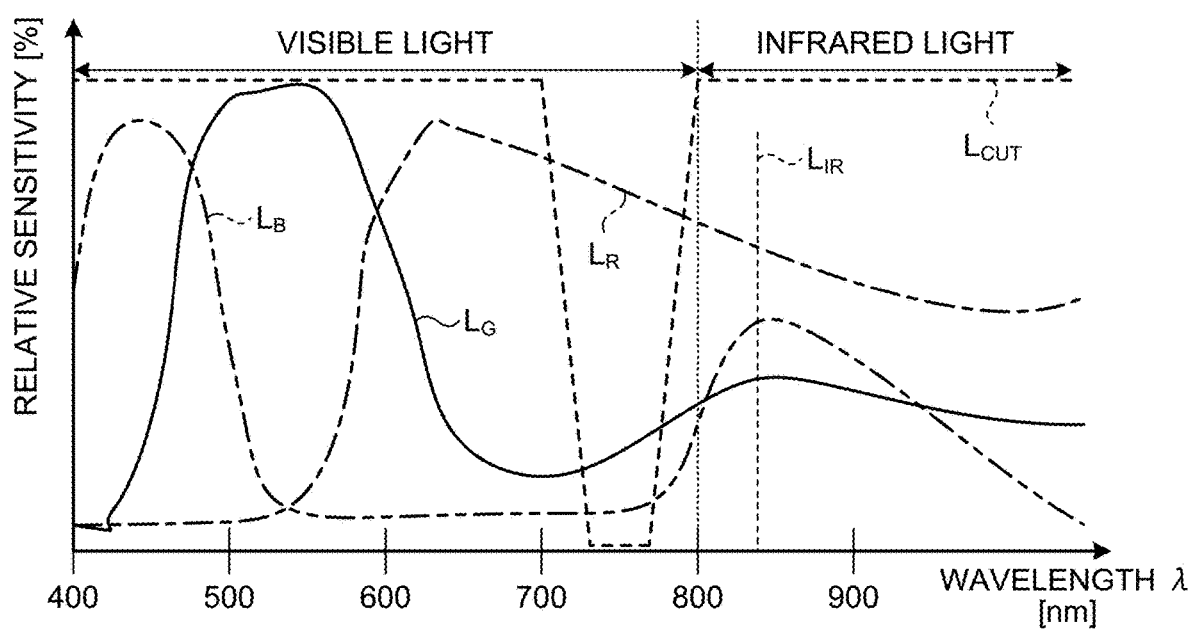
FIG. 5 is a diagram schematically illustrating the sensitivity of an image sensor in each wavelength band after passing through the color filter according to the first embodiment.

Here, a spectral characteristic of each pixel will be described. FIG. 5 is a diagram schematically illustrating the sensitivity of the image sensor in each wavelength band after passing through the color filter. In FIG. 5, the horizontal axis represents wavelength (nm) and the vertical axis represents spectral characteristic. Furthermore, in FIG. 5, a curve $L_B$ represents a spectral characteristic of the B pixel, a curve $L_G$ represents a spectral characteristic of the G pixel, a curve $L_R$ represents a spectral characteristic of the R pixel, and a straight line $L_{IR}$ represents a wavelength band of fluorescence generated by irradiating a fluorescent substance with excitation light. A curve $L_{CUT}$ represents a transmission characteristic of the cut filter 213.

As represented by the curve $L_B$ and the straight line $L_{IR}$ of FIG. 5, the B pixel is sensitive to light in the blue wavelength band (435 nm to 480 nm) (hereinafter, simply referred to as "blue light") and is sensitive to fluorescence in a wavelength band (830±10 nm) generated by irradiating the fluorescent substance with excitation light. Furthermore, as represented by the curve line $L_G$ and the straight line $L_{IR}$ of FIG. 5, the G pixel (Gr pixel and Gb pixel) is sensitive to light in the green wavelength band (500 nm to 560 nm) (hereinafter, simply referred to as "green light") and is sensitive to fluorescence in the wavelength band (830±10 nm) generated by irradiating the fluorescent substance with excitation light. Furthermore, as represented by the curve line $L_R$ and the straight line $L_{IR}$ of FIG. 5, the R pixel is sensitive to light in the red wavelength band (610 nm to 750 nm) (hereinafter, simply referred to as "red light") and is sensitive to fluorescence in the wavelength band (830±10 nm) generated by irradiating the fluorescent substance with excitation light.

The light emitting unit 22 includes an illumination optical system configured by using one or more lenses. The light emitting unit 22 emits illumination light in the same direction as an imaging direction of the imaging unit 21, the illumination light being at least one of white light supplied from the light source device 3 via the light guide 4, light in a red wavelength band, light in a green wavelength band, light in a blue wavelength band, and infrared light. Note that the light emitting unit 22 may be provided with a light emitting diode (LED), a laser light source, or the like at the microscope unit 5 to omit optical transmission via the light guide or the like.

The detection unit 23 sequentially detects status information about the observation device 2. The status information about the observation device 2 includes information about position, focus, and zoom information about the imaging unit 21. The detection unit 23 includes various sensors to detect such information.

The input unit 24 receives input of an operation instruction to the imaging unit 21. The input unit 24 includes a focus switch and a zoom switch each configured to receive an input of an instruction for focus or zoom operation in the imaging unit 21, an electric scrolling mode switch configured to receive an input of an instruction for an electric scrolling mode, and a mode changeover switch configured to receive input of instruction for changing an observation mode of the medical observation system 1. As illustrated in FIG. 1, various switches, buttons, and the like constituting the input unit 24 are provided on the side surface of the microscope unit 5.

The first control unit 25 controls the operation of the imaging unit 21 in response to an operation instruction received by the input unit 24 or an operation instruction input from the control device 9 which is described later. Furthermore, the first control unit 25 integrally controls the observation device 2 in cooperation with a second control unit 94 of the control device 9 which is described later. The first control unit 25 includes a memory, and a processor such as a CPU, FPGA, or ASIC.

Configuration of Light Source Device

A configuration of the light source device 3 will be described next.

The light source device 3 includes a first light source unit 31, a second light source unit 32, a third light source unit 33, and a fourth light source unit 34.

Under the control by the control device 9, the first light source unit 31 supplies red light to the light emitting unit 22 of the observation device 2 via the light guide 4. The first light source unit 31 is achieved by using a red LED or the like.

Under the control by the control device 9, the second light source unit 32 supplies green light to the light emitting unit 22 of the observation device 2 via the light guide 4. The second light source unit 32 is achieved by using a green LED or the like.

Under the control by the control device 9, the third light source unit 33 supplies blue light to the light emitting unit 22 of the observation device 2 via the light guide 4. The third light source unit 33 is achieved by using a blue LED or the like.

The fourth light source unit 34 supplies infrared light exciting the fluorescent substance to the light emitting unit 22 of the observation device 2 via the light guide 4. Under the control by the control device 9, the fourth light source unit 34 supplies infrared light (in a wavelength band of 740±10 nm) functioning as excitation light exciting the fluorescent substance. The second light source unit 32 includes a semiconductor laser device configured to be able to emit infrared light (700 to 1000 nm) used for indocyanine green (ICG) observation, a filter configured to transmit only a predetermined wavelength band (a wavelength band of 740±10 nm), and the like. Note that in the following, infrared light is described, but the excitation light is not limited to this, and, for example, light (a wavelength band of 415±10 nm) used for photo dynamic diagnosis (PDD) observation of fluorescence of a photosensitive substance, such as hematoporphyrin derivative, accumulated in tumor tissue in advance may be employed, and light (a wavelength band of 390 to 470 nm+a wavelength band of 540 to 560 nm) used for auto fluorescence imaging (AFI) for observation of auto fluorescence from a fluorescent substance such as collagen may be employed.

Configuration of Control Device

Next, the functional configuration of the control device 9 will be described.

The control device 9 includes an image processing unit 91, an input unit 92, a recording unit 93, and the second control unit 94.

The image processing unit 91 performs various image processing on image data transmitted from the observation device 2 to generate an image to be displayed (video data) that is displayed by the display device 8. Here, examples of the image processing include various image processing and the like, such as color correction, color enhancement, and contour enhancement. Furthermore, the image processing unit 91 generates an interpolation pixel value based on a first pixel value included in image data transmitted from the observation device 2, generates a background image based on the first pixel value and the interpolation pixel value, and generates a fluorescence image based on a second pixel value included in the image data transmitted from the observation device 2. The interpolation pixel value corresponds to a component of the second visible light (blue light) that is in a band different from that of the first visible light (one of red light and green light), the first pixel value is output from a pixel receiving the first visible light (one of red light and green light), and the second pixel value is output from a pixel receiving fluorescence. The image processing unit 91 includes a memory and a processor such as a graphics processing unit (GPU), ASIC, or FPGA. The image processing unit 91 includes at least a subtraction unit 911, a first generation unit 912, a second generation unit 913, a third generation unit 914, and a combining unit 915.

The subtraction unit 911 subtracts the second pixel value from the first or third pixel value included in image data input from the imaging unit 21, and outputs a result of the subtraction to the second generation unit 913. The second pixel value is output from a pixel (B pixel) on which the second filter (filter B) is arranged, and the first or third pixel value is output from a pixel (R pixel or G pixel) on which the first or third filter (filter R or filter G) is arranged. Specifically, the subtraction unit 911 may divide the spectral sensitivity of the fluorescence wavelength of the first or third filter, by the spectral sensitivity of the fluorescence wavelength of the second filter to obtain a divided value, multiply the divided value by the second pixel value to obtain a multiplication result, subtract the multiplication result from the first or third pixel value to obtain a subtraction result, and output the subtraction result to the second generation unit 913. Note that the calculation method by the subtraction unit 911 will be described later.

Under the control by the second control unit 94, the first generation unit 912 generates a fluorescence image based on the second pixel value included in the image data input from the imaging unit 21 and outputs the fluorescence image to the combining unit 915. The second pixel value is output from a pixel (B pixel) on which the second filter (filter B) is arranged. Specifically, the first generation unit 912 generates the fluorescence image by interpolating the pixel values of the R pixel and the G pixel, based on the pixel value of the B pixel included in the image data, and outputs the fluorescence image to the combining unit 915. Furthermore, the first generation unit 912 performs colorization for the fluorescence image. Specifically, the first generation unit 912 colorizes the fluorescence image by a tone conversion process or the like based on the brightness value of the fluorescence image, and outputs the colored fluorescence image to the combining unit 915. For example, the first generation unit 912 performs the colorization to color a fluorescent area green based on the brightness value of the fluorescence image. Note that the first generation unit 912 may set a colorization color to the fluorescence image, based on a designation signal input from the input unit 92 via the second control unit 94 to specify the color of the fluorescent area of the fluorescence image.

Under the control by the second control unit 94, the second generation unit 913 generates a first background image, based on the first or third pixel value included in the image data input from the imaging unit 21 and outputs the first background image to the third generation unit 914. The first or third pixel value is output from a pixel (R pixel or G pixel) on which the first or third filter (filter R or filter G) is arranged. Specifically, the second generation unit 913 generates the first background image based on a result of the input from the subtraction unit 911. Furthermore, the second generation unit 913 generates the interpolation pixel value based on the first or third pixel value included in the image data input from the imaging unit 21 and outputs the interpolation pixel value to the third generation unit 914. The first or third pixel value is output from a pixel (R pixel or G pixel) on which the first or third filter (filter R or filter G) is arranged, and the interpolation pixel value interpolates a pixel value corresponding to a component of one of red, green, and blue light that is not included in the visible light.

The third generation unit 914 generates a second background image based on the interpolation pixel value and the first or third pixel value (the first background image) that are input from the second generation unit 913 and outputs the second background image to the combining unit 915. Furthermore, the third generation unit 914 may perform binarization for the second background image and output the second background image to the combining unit 915. For example, the third generation unit 914 may perform a saturation reduction process to reduce the saturation of the background image and output the binarized second background image to the combining unit 915.

The combining unit 915 generates a composite image in which the fluorescence image input from the first generation unit 912 and the second background image input from the third generation unit 914 are combined, and outputs the composite image to the display device 8. Specifically, the combining unit 915 generates the composite image by combining the fluorescence image with the second background image at a predetermined ratio (e.g., 1:1).

The input unit 92 includes a user interface such as a keyboard, mouse, touch panel, and foot switch, and receives input of various information.

The recording unit 93 is constituted by using a semiconductor memory such as a flash memory or dynamic random access memory (DRAM) and includes a program recording unit 931 configured to temporarily record various programs executed by the medical observation system 1 and data being processed.

The second control unit 94 integrally controls the respective units of the medical observation system 1. The second control unit 94 is achieved by using a general-purpose processor, such as a CPU having an internal memory (not illustrated) in which a program is recorded, or a dedicated processor having various arithmetic circuits, such as an ASIC, for performing a specific function. Furthermore, the second control unit 94 may include an FPGA that is a type of a programmable integrated circuit. Note that when the FPGA is included, a memory for storing configuration data may be provided so that the FPGA as the programmable integrated circuit is configured based on the configuration data read from the memory.

Processing of Medical Observation System

Figure 6:
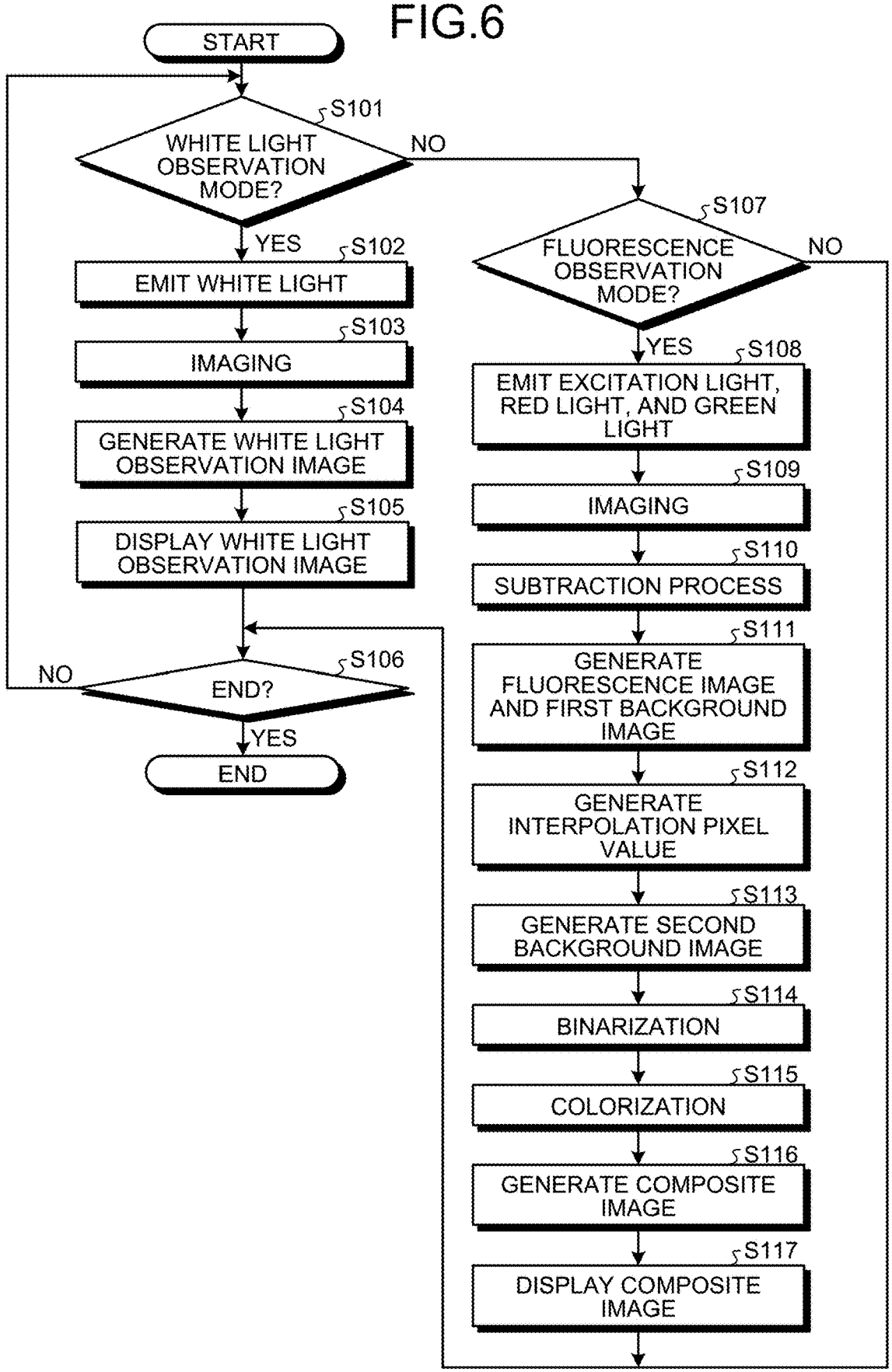
FIG. 6 is a flowchart illustrating the outline of a process performed by the medical observation system according to the first embodiment.

Next, a process performed by the medical observation system 1 will be described. FIG. 6 is a flowchart illustrating the outline of the process performed by the medical observation system 1.

As illustrated in FIG. 6, the second control unit 94 determines whether the medical observation system 1 is set to a white light observation mode in which white light is emitted to an object (Step S101). If the second control unit 94 determines that the medical observation system 1 is set to the white light observation mode in which white light is emitted to the object (Step S101: Yes), the medical observation system 1 proceeds to Step S102 which is described later. On the other hand, if the second control unit 94 determines that the medical observation system 1 is not set to the white light observation mode in which white light is emitted to the object (Step S101: No), the medical observation system 1 proceeds to Step S107 which is described later.

In Step S102, the second control unit 94 causes the first light source unit 31, the second light source unit 32, and the third light source unit 33 to emit white light.

At this time, the fourth light source unit 34 is turned off.

Next, the second control unit 94 controls the first control unit 25 to cause the imaging unit 21 to receive reflected light from an object to capture an image (Step S103).

Then, the image processing unit 91 performs various image processing on image data input from the imaging unit 21 to generate a white light observation image (Step S104).

Subsequently, the display device 8 displays the white light observation image input from the image processing unit 91 (Step S105). This makes it possible for a user such as a doctor to observe an object to be observed.

Then, the second control unit 94 determines whether an instruction signal for terminating the observation of the object to be observed is input from the input unit 92 (Step S106). If it is determined by the second control unit 94 that the instruction signal for terminating the observation of the object to be observed is input from the input unit 92 (Step S106: Yes), the medical observation system 1 finishes this process. On the other hand, if it is determined that no instruction signal for terminating the observation of the object to be observed is input from the input unit 92 (Step S106: No), the medical observation system 1 returns to Step S101 described above.

In Step S107, the second control unit 94 determines whether the medical observation system 1 is set to a fluorescence observation mode for emitting at least excitation light to the object (Step S107). If the second control unit 94 determines that the medical observation system 1 is set to the fluorescence observation mode for emitting at least excitation light to the object (Step S107: Yes), the medical observation system 1 proceeds to Step S108 which is described later. On the other hand, if the second control unit 94 determines that the medical observation system 1 is not set to the fluorescence observation mode for emitting at least excitation light to the object (Step S107: No), the medical observation system 1 proceeds to Step S106.

Figure 7:
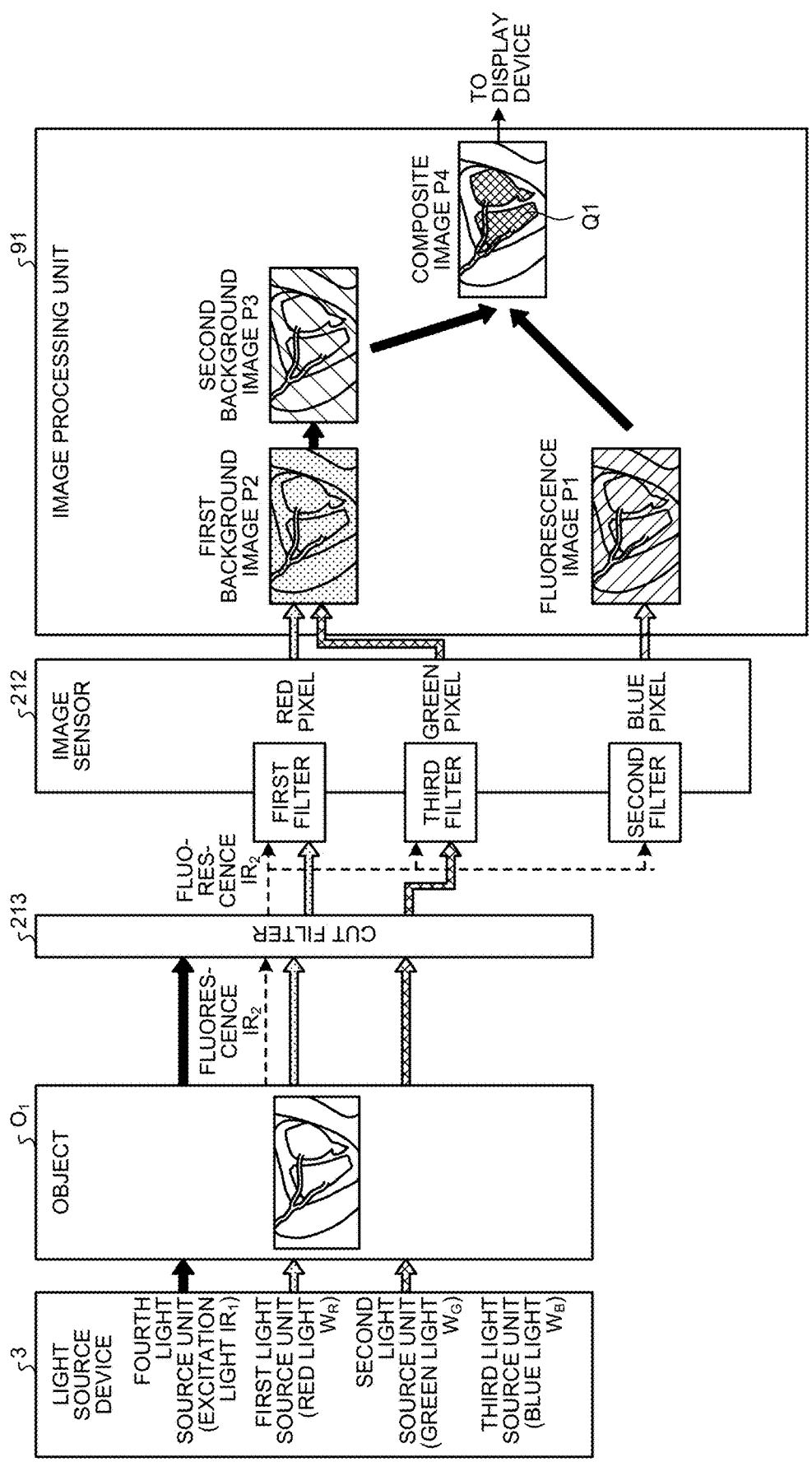
FIG. 7 is a diagram schematically illustrating the outline of a process in a fluorescence observation mode performed by the medical observation system according to the first embodiment.

In Step S108, the second control unit 94 causes the fourth light source unit 34 to emit excitation light to the object to which a fluorescent substance is administered, causing the first light source unit 31 and the second light source unit 32 to emit light to irradiate the object with red light and green light (Step S108). Specifically, as illustrated in FIG. 7, the second control unit 94 causes the fourth light source unit 34 in the light source device 3 to emit excitation light IR' to the object $O_1$ to which the fluorescent substance has been administered. In this case, the second control unit 94 causes the first light source unit 31 and the second light source unit 32 to emit light at the same time as the fourth light source unit 34, thereby emitting the excitation light IR', red light $W_R$, and green light $W_G$ to the object $O_1$. Furthermore, the third light source unit 33 is turned off.

Next, the second control unit 94 causes the imaging unit 21 to receive fluorescence $IR_2$ emitted from the object $O_1$ to capture an image, and causes the imaging unit 21 to receive light returned from the object $O_1$ or red light $W_R$ and green light $W_G$ that are reflected light from the object $O_1$ to capture an image (Step S109). In this case, as illustrated in FIG. 7, the cut filter 213 blocks the excitation light $IR_1$ reflected from the object $O_1$ and transmits the fluorescence $IR_2$, red light $W_R$, and green light $W_G$ from the object $O_1$. Furthermore, in the respective pixels (the R pixels, G pixels, and B pixels) in the image sensor 212, the filters (the filters R, filters G, and filters B) are sensitive to the infrared range. Therefore, the light source device 3 emits no red light and the excitation light $IR_1$ is blocked by the cut filter 213, and thereby, only the fluorescence $IR_2$ is incident on the B pixels of the image sensor 212. Furthermore, the fluorescence $IR_2$ and the red light $W_R$ that is reflected from the object $O_1$ are incident on the R pixels of the image sensor 212. Furthermore, the fluorescence $IR_2$ and the green light $W_G$ that is reflected from the object $O_1$ are incident on the G pixels of the image sensor 212. At this time, in a pixel value output from each of the R pixels and the G pixels, because the intensity of the fluorescence $IR_2$ incident on each of the R pixels and the G pixels is weaker than the intensities of the reflected red light and the reflected green light, the reflected red light and reflected green light dominate. Furthermore, no blue light is emitted from the light source device 3, and thus, the pixel value of each B pixel is dominated by the fluorescence $IR_2$. In other words, the image processing unit 91 may use an output value of the B pixel as an output value of the fluorescence $IR_2$, and output values of the R pixel and the G pixel may be used as output values of visible light (reflected red light and reflected green light).

Then, the subtraction unit 911 performs a subtraction process for subtracting the second pixel value from the first or third pixel value included in the image data input from the imaging unit 21 (Step S110). The second pixel value is output from a pixel (B pixel) on which the second filter (filter B) is arranged, and the first or third pixel value is output from a pixel (R pixel or G pixel) on which the first or third filter (filter R or filter G) is arranged.

Here, the subtraction process performed by the subtraction unit 911 will be described in detail.

When the value of a fluorescent component included in a pixel value output from a Gr pixel (hereinafter, simply referred to as "IRgr"), the value of a fluorescent component included in a pixel value output from a Gb pixel (hereinafter, simply referred to as "IRgb"), and the value of a fluorescent component included in a pixel value output from an R pixel (hereinafter, simply referred to as "IRr") are obtained, a pixel value from which the fluorescent component of each pixel is removed may be estimated from the value of a fluorescent component included in a pixel value output from a B pixel (hereinafter, simply referred to as "IRb"). Specifically, when the spectral sensitivities of the R pixel, G pixel (Gr pixel, Gb pixel), and B pixel on the straight line $L_{IR}$ of FIG. 5 are defined as r, g, and b [%], the fluorescent components input to each of the R pixel, G pixel (Gr pixel, Gb pixel), and B pixel are considered to be constant. Therefore, the following formulas hold.

$$IRgr \approx IRgb \approx (g/b)*IRb \quad (1)$$

$$IRr \approx (r/b)*IRb \quad (2)$$

Furthermore, the light source device 3 emits no blue light, and thus, the pixel value of the B pixel=IRb. Therefore, when the pixel value of the R pixel is R, the pixel value of the Gr pixel is Gr, the pixel value of the Gb pixel is Gb, and the pixel value of the B pixel is B, the subtraction unit 911 uses the following formulas (3) to (5) to calculate a value by subtracting the value of the fluorescent component from each of the pixel value of the R pixel and pixel value of the G pixel.

$$\text{Pixel value of } Gr \text{ pixel}=Gr-(g/b)*IRgr \approx Gr-(g/b)*B \quad (3)$$

$$\text{Pixel value of } Gb \text{ pixel}=Gb-(g/b)*IRgb \approx Gb-(g/b)*B \quad (4)$$

$$\text{Pixel value of } R \text{ pixel}=R-(r/b)*IRr \approx R-(r/b)*B \quad (5)$$

Next, under the control by the second control unit 94, the image processing unit 91 generates a fluorescence image and a first background image (Step S111). Specifically, the first generation unit 912 uses a pixel value of each B pixel included in the image data input from the image sensor 212 to generate the fluorescence image. In this case, as illustrated in FIG. 7, the first generation unit 912 generates a fluorescence image P1 in which the pixel value of each B pixel is used to interpolate a pixel value corresponding to the position of each of the R pixels and G pixels. This fluorescence image P1 is a fluorescence intensity image. Furthermore, the second generation unit 913 uses the pixel value of each of the R pixels and G pixels included in the image data and generates a first background image P2. The image data is input from the image sensor 212 and then input from the subtraction unit 911. In this case, as illustrated in FIG. 7, the second generation unit 913 uses the pixel values of each of the R pixels and B pixels to generate the first background image P2 in which the pixel value corresponding to the position of each B pixel is interpolated. This first background image P2 has only a red and a green components and has no blue component that has been present in white light observation, and thus, for example, when the pixel value of the B pixel is set to black to generate the first background image P2 and then an image is generated on the first background image P2 by demosaic processing, the image has unnatural color. Therefore, the first background image P2 illustrated in FIG. 7 is hatched in order to show an unnatural color.

Then, the image processing unit 91 generates an interpolation image value in which the pixel value of a B pixel is interpolated (Step S112). Specifically, the second generation unit 913 generates the interpolation pixel value based on the first or third pixel value included in the image data input from the subtraction unit 911. The first or third pixel value is output from a pixel (R pixel or G pixel) on which the first or third filter (filter R or filter G) is arranged, and in the interpolation pixel value, a pixel value corresponding to a component of one of red, green, and blue light that is not included in the visible light emitted from the light source device 3 is interpolated. For example, the second generation unit 913 generates an interpolation pixel value in which a pixel value corresponding to the component of blue light output from each B pixel is interpolated, based on a third pixel value output from a G pixel, and outputs the interpolation pixel value to the third generation unit 914. Note that the second generation unit 913 may generate an interpolation pixel value in which a pixel value corresponding to the component of blue light output from each B pixel is interpolated, based on a first pixel value output from an R pixel, and outputs the interpolation pixel value to the third generation unit 914.

Figure 8A:
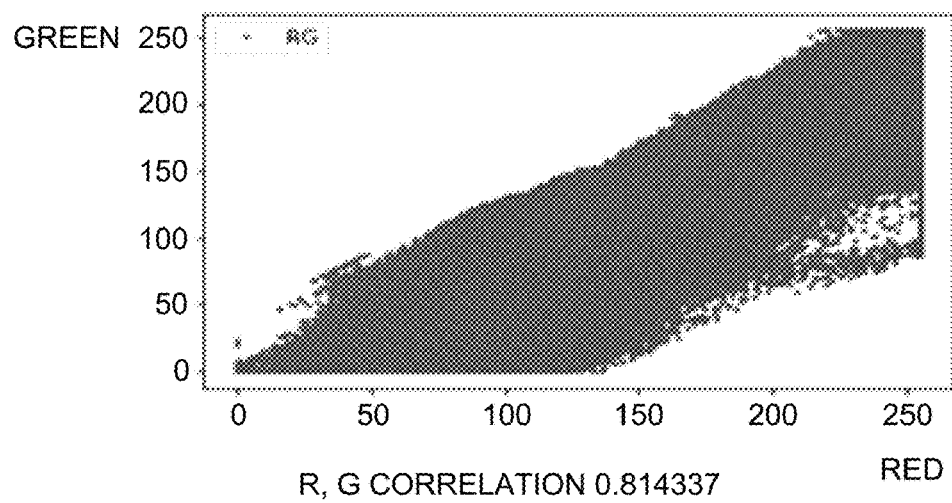
FIG. 8A is a graph illustrating a correlation between pixels located at the same positions of a red image, a green image, and a blue image that are obtained by separating a medical image of a surgical site (biological tissue) of a subject.
Figure 8B:
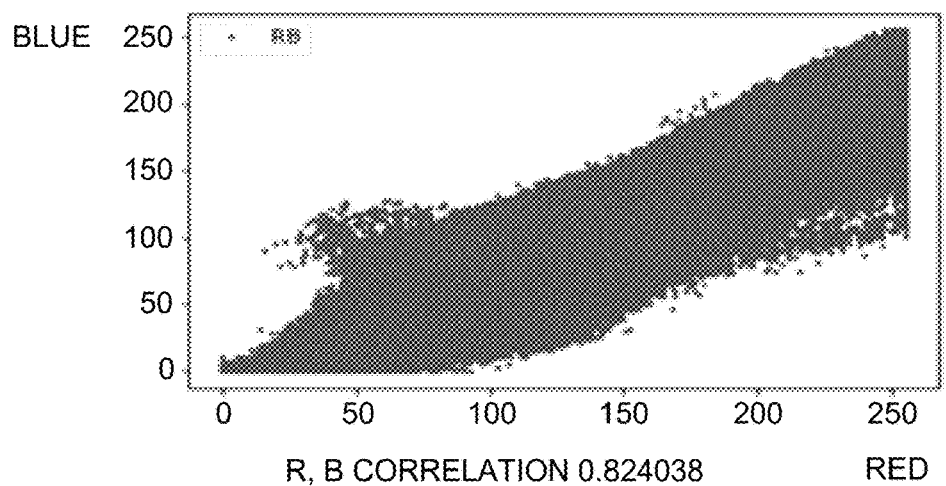
FIG. 8B is a graph illustrating a correlation between pixels located at the same positions of the red image, the green image, and the blue image that are obtained by separating the medical image of the surgical site (biological tissue) of the subject.
Figure 8C:
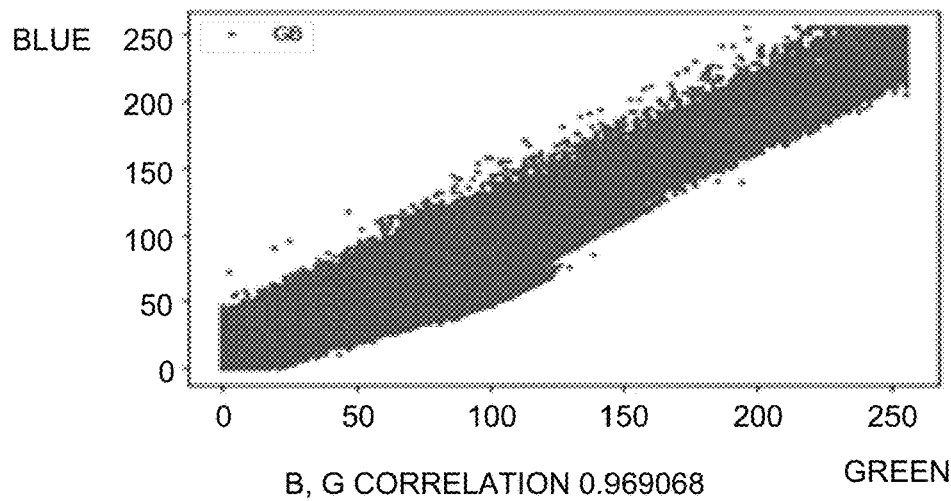
FIG. 8C is a graph illustrating a correlation between pixels located at the same positions of the red image, the green image, and the blue image that are obtained by separating the medical image of the surgical site (biological tissue) of the subject.
Figure 9A:
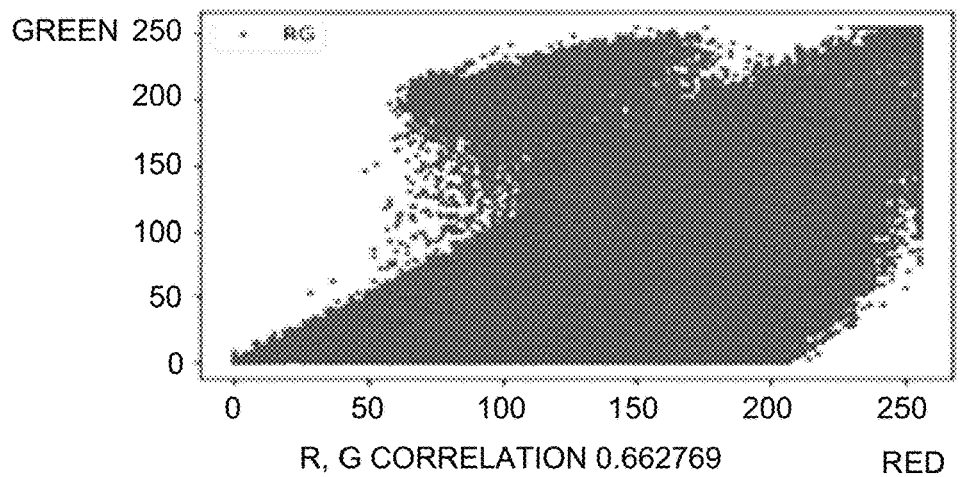
FIG. 9A is a graph illustrating a correlation between pixels located at the same positions of a red image, a green image, and a blue image that are obtained by separating another medical image of a surgical site (biological tissue) of a subject.
Figure 9B:
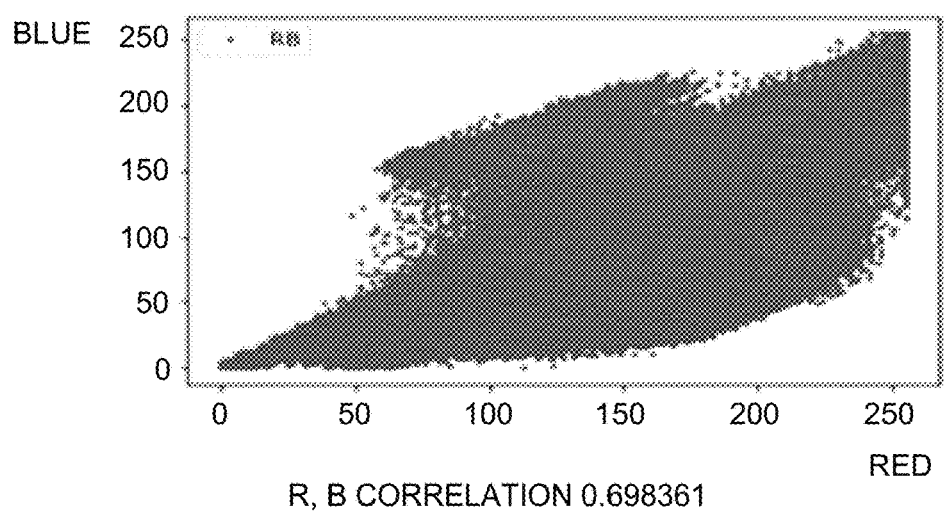
FIG. 9B is a graph illustrating a correlation between pixels located at the same positions of the red image, the green image, and the blue image that are obtained by separating the another medical image of the surgical site (biological tissue) of the subject.
Figure 9C:
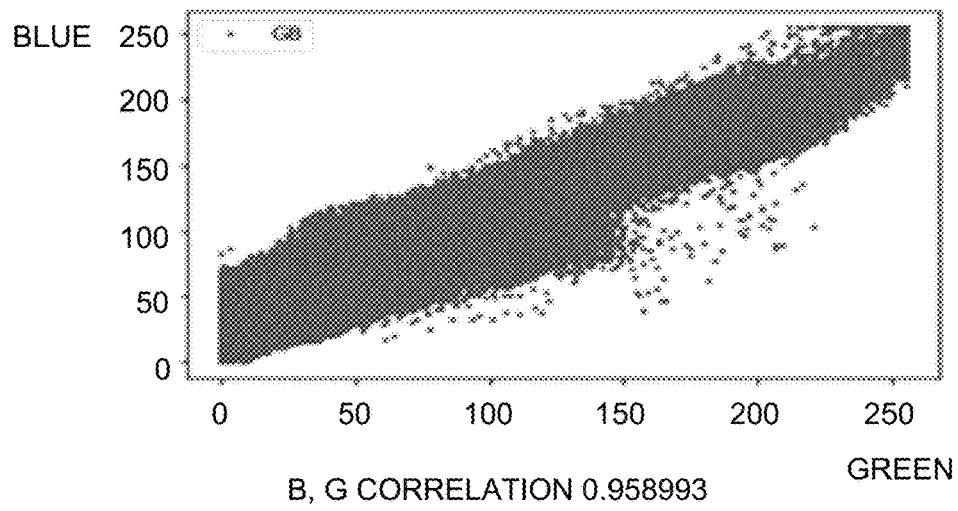
FIG. 9C is a graph illustrating a correlation between pixels located at the same positions of the red image, the green image, and the blue image that are obtained by separating the another medical image of the surgical site (biological tissue) of the subject.

Here, an interpolation method of interpolation by the second generation unit 913 will be described. FIGS. 8A to 8C are each a graph illustrating a correlation between pixels located at the same positions of a red image, green image, and blue image that are obtained by separating a medical image of a surgical site (biological tissue) of a subject. FIGS. 9A to 9C are each a graph illustrating a correlation between pixels located at the same positions of a red image, green image, and blue image that are obtained by separating another medical image of a surgical site (biological tissue) of the subject. FIG. 10 is a table illustrating a correlation between pixels located at the same positions of red images, green images, and blue images that are obtained by separating a plurality of medical images of a surgical site (biological tissue) of the subject.

Images of a surgical site captured for medical use show blood, fat, or the like, and thus, are dominated by colors of red, yellow, and white. Therefore, as illustrated in FIGS. 8A to 8C, 9A to 9C, and Table T1 of FIG. 10, when the images captured for medical use are separated into a red image, a green image, and a blue image and correlated at the same position of the respective images, a correlation between a G pixel and a B pixel is much higher than the other correlations. Therefore, the second generation unit 913 generates an interpolation pixel value of a B pixel by interpolating the pixel value of the B pixel to be interpolated, from the pixel value of a G pixel located in the vicinity of the B pixel. Specifically, the second generation unit 913 generates the interpolation pixel value of a target B pixel (B pixel of interest) by using the following methods 1 to 6 or the like.

Method 1: A value obtained by replicating the pixel value of a Gr pixel adjacent to the target B pixel is used as the interpolation pixel value.

Method 2: A value obtained by replicating the pixel value of a Gb pixel adjacent to the target B pixel is used as the interpolation pixel value.

Method 3: An average value of pixel values of a Gr pixel and a Gb pixel that are adjacent to the target B pixel is used as the interpolation pixel value.

Method 4: A larger pixel value obtained after comparison between pixel values of a Gr pixel and Gb pixel adjacent to the target B pixel is used as the interpolation pixel value.

Method 5: A smaller pixel value obtained after comparison between pixel values of a Gr pixel and Gb pixel adjacent to the target B pixel is used as the interpolation pixel value.

Method 6: An average value of pixel values of a plurality of Gr pixels and Gb pixels located in a predetermined range (e.g., 3×3 pixels) around the target B pixel is used as the interpolation pixel value.

Figure 11:
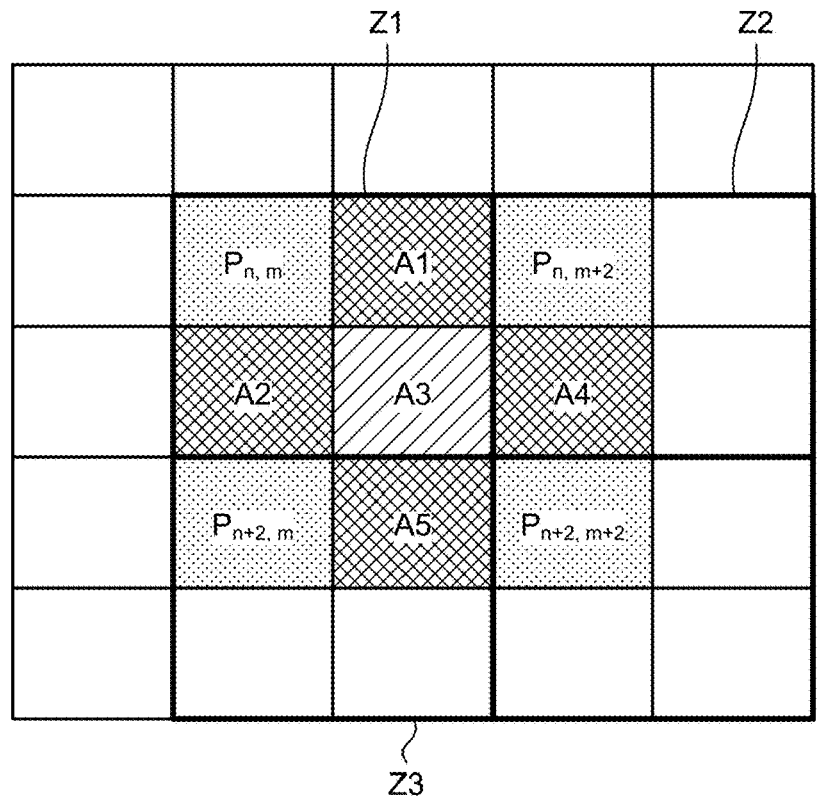
FIG. 11 is a diagram schematically illustrating a generation method for generating a fluorescence image by a first generation unit according to the first embodiment.

Here, a generation method for generating the fluorescence image P1 by the first generation unit 912 will be described. FIG. 11 is a diagram schematically illustrating the generation method for generating the fluorescence image P1 by the first generation unit 912.

As illustrated in FIG. 11, the first generation unit 912 interpolates a pixel value corresponding to the position of each of an R pixel and G pixels by replicating the pixel value of the B pixel (pixel $P_{n,m}$) as the pixel values of the R pixel (A3) and G pixels (A1, A2), without using the pixel value of each of the R pixel (A3) and G pixels (A1, A2) in a unit Z1 in a Bayer array, which is included in image data input from the image sensor 212. Likewise, in a unit Z2, the first generation unit 912 replicates the pixel value of a B pixel (pixel $P_{n,m+2}$) as the pixel values of an R pixel and G pixel (e.g., A4) to interpolate the pixel value corresponding to the position of each of the R pixel and G pixel. Furthermore, in a unit Z3, the first generation unit 912 replicates the pixel value of a B pixel (pixel $P_{n+2,m}$) as the pixel value of an R pixel and G pixel (e.g., A5) to interpolate the pixel value corresponding to the position of each of the R pixel and G pixel. In this way, the first generation unit 912 uses the pixel value of a B pixel in each unit to generate the fluorescence image P1 in which the pixel value corresponding to the position of each of the R pixel and G pixel is interpolated.

Figure 12:
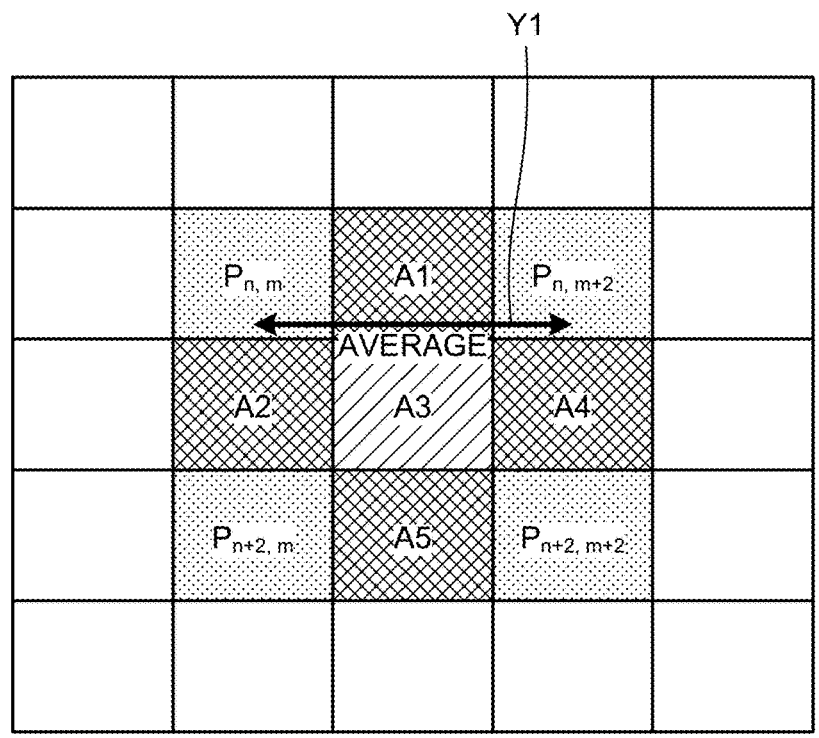
FIG. 12 is a schematic diagram illustrating another example of the generation method for generating a fluorescence image by the first generation unit according to the first embodiment.

FIG. 12 is a schematic diagram illustrating another example of the generation method for generating the fluorescence image P1 by the first generation unit 912.

As illustrated in FIG. 12, the first generation unit 912 uses an average value of the pixel values of adjacent B pixels to interpolate the pixel value corresponding to the position of each of the R pixel and the G pixels, and generates the fluorescence image P1. Specifically, the first generation unit 912 sets the pixel value of a G pixel (A1) to an average value ((pixel value of pixel $P_{n,m}$)+(pixel value of pixel $P_{n,m+2}$)/2) of the pixel value of a B pixel (pixel $P_{n,m}$) and the pixel value of a B pixel (pixel $P_{n,m+2}$) that are adjacent to the G pixel. Likewise, the first generation unit 912 sets the pixel value of a G pixel (A2) to an average value ((pixel value of pixel $P_{n+2,m}$)+(pixel value of pixel $P_{n,m}$)/2) of the pixel value of a B pixel (pixel $P_{n,m}$) and the pixel value of a B pixel (pixel $P_{n+2,m}$) that are adjacent to the G pixel. Furthermore, the first generation unit 912 sets the pixel value of an R pixel (A3) to an average value ((pixel value of pixel $P_{n2,m}$)+(pixel value of pixel $P_{n+2,m+2}$)/2) of the pixel value of a B pixel (pixel $P_{n,m}$) and the pixel value of a B pixel (pixel $P_{n+2,m+2}$) that are adjacent to the R pixel. In this way, the first generation unit 912 uses an average value of the pixel values of adjacent B pixels to interpolate the pixel value corresponding to the position of each of the R pixel and G pixels, and generates the fluorescence image P1.

Figure 13:
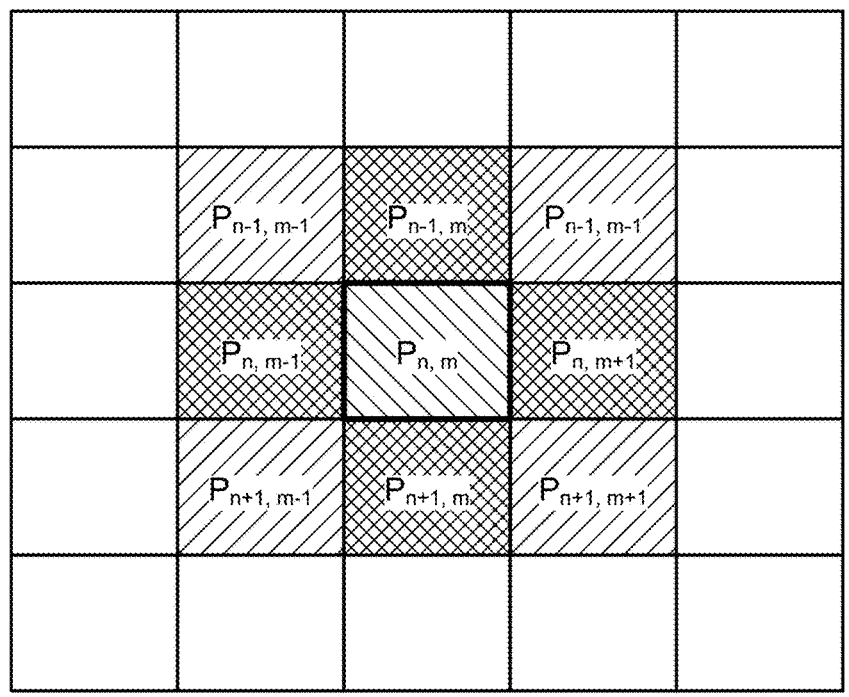
FIG. 13 is a diagram schematically illustrating a generation method for generating a background image by a second generation unit according to the first embodiment.

FIG. 13 is a diagram schematically illustrating a generation method for generating the first background image P2 by the second generation unit 913.

As illustrated in FIG. 13, the second generation unit 913 considers a B pixel (pixel $P_{n,m}$) as black color (pixel value is 0) and generates the first background image P2.

Returning to FIG. 6, the description will be continued from Step S113.

In Step S113, the third generation unit 914 generates a second background image based on the interpolation pixel value and the first background image that are input from the second generation unit 913. Specifically, as illustrated in FIG. 7, the third generation unit 914 combines the interpolation pixel value and the first background image P2 that are input from the second generation unit 913, performs demosaic processing, and generates a second background image P3. Thus, the second background image P3 has a color closer to the color in white light observation.

Subsequently, the third generation unit 914 may perform binarization for the second background image P3 and output the second background image P3 to the combining unit 915 (Step S114). Specifically, the third generation unit 914 may perform grayscale processing on the second background image P3 to generate a grayscale image and outputs the grayscale image to the combining unit 915.

Then, the first generation unit 912 performs colorization for the fluorescence image P1 and outputs the fluorescence image P1 to the combining unit 915 (Step S115). Specifically, the first generation unit 912 colorizes the fluorescence image P1 by a tone conversion process or the like based on the brightness value of the fluorescence image P1, and outputs the colored fluorescence image P1 to the combining unit 915. For example, the first generation unit 912 colorizes the fluorescence image P1 green.

Then, the combining unit 915 generates a composite image P4 in which the fluorescence image P1 generated by the first generation unit 912 and the second background image P3 generated by the third generation unit 914 are combined (Step S116). Specifically, as illustrated in FIG. 7, the combining unit 915 generates the composite image P4 in which the fluorescence image P1 and the second background image P3 (background image) are combined, and outputs the composite image P4 to the display device 8. In this case, the combining unit 915 generates the composite image P4 by combining the fluorescence image P1 with the second background image P3 at a predetermined ratio (e.g., 1:1).

Then, the display device 8 displays the composite image P4 input from the combining unit 915 (Step S117). Thus, as illustrated in FIG. 7, the user such as a doctor may grasp the position of a fluorescent area Q1 by observing the composite image P4 of a color closer to natural color that is displayed on the display device 8. After Step S117, the medical observation system 1 proceeds to Step S106.

According to the first embodiment described above, the image processing unit 91 generates the interpolation pixel value in which a pixel value corresponding to the component of blue light is interpolated, based on the first or third pixel value (R pixel or G pixel), generates the background image (second background image) corresponding to each component of light in red, green, and blue wavelength bands, based on the first or third pixel value and the interpolation pixel value, and generates the fluorescence image, based on the second pixel value. The first or third pixel value is included in image data and output from a pixel on which the first or third filter (filter R or filter G) is arranged, and the second pixel value is included in the image data and output from a pixel on which the second filter (filter B) is arranged. In this method, visible light and infrared excitation light are preferably emitted from the light source device 3 at the same time, and it is not necessary to alternately emit the visible light and infrared excitation light, and thus flickering of an observed region of an object to be observed may be prevented and the size of the device may be reduced.

Furthermore, according to the first embodiment, the fluorescence image P1 and the normal white light observation image are allowed to be generated by using one image sensor 212 having a normal Bayer array, and thus observation of the observed region of the object to be observed is possible while appropriately switching between the white light observation mode and the fluorescence observation mode, without using a special image sensor.

Furthermore, in the first embodiment, the image processing unit 91 generates the pixel value of a B pixel as the interpolation pixel value, based on the pixel value of a G pixel, and thus it becomes possible to generate the background image (second background image) having a color closer to that of the white light observation.

Furthermore, according to the first embodiment, after binarization for the background image (second background image), the image processing unit 91 combines the binarized background image (second background image) with the fluorescence image, and thereby it is possible to emphasize the fluorescent area on the composite image.

Furthermore, according to the first embodiment, after colorization of the fluorescence image, the image processing unit 91 combines the colorized fluorescence image with the background image (second background image), and thus, it is possible to emphasize the fluorescent area on the composite image.

Furthermore, according to the first embodiment, when the medical observation system 1 is set to the white light observation mode, the second control unit 94 causes the first light source unit 31, the second light source unit 32, and the third light source unit 33 to emit white light, and when the medical observation system 1 is set to the fluorescence observation mode, the second control unit 94 causes the first light source unit 31, the second light source unit 32, and the fourth light source unit 34 to simultaneously emit visible light and excitation light, and thus, it is possible to observe the observed region of the object to be observed while appropriately switching between the white light observation mode and the fluorescence observation mode.

Furthermore, according to the first embodiment, the image processing unit 91 divides the spectral sensitivity of the first filter (filter R, filter G) by the spectral sensitivity of the second filter (filter B) to obtain a divided value, multiplies the divided value by the second pixel value (pixel value of the B pixel) to obtain a multiplication result, subtracts the multiplication result from the first pixel value (pixel value of each of the R pixel and G pixel) to obtain a subtraction result, and generates the background image based on the subtraction result. Therefore, it is possible to generate the background image from which the fluorescent component is removed.

Note that in the first embodiment, the image processing unit 91 divides the spectral sensitivity of a fluorescence wavelength of the first filter (filter R, filter G) by the spectral sensitivity of a fluorescence wavelength of the second filter (filter B) to obtain a divided value, multiplies the divided value by the second pixel value (pixel value of the B pixel) to obtain a multiplication result, and subtracts the multiplication result from the first pixel value (pixel value of each of the R pixel and G pixel), but the second pixel value may merely be subtracted from the first pixel value.

Furthermore, in the first embodiment, when the medical observation system 1 is set to the fluorescence observation mode, the second control unit 94 causes each of the second light source unit 32 and the third light source unit 33 to emit light, but the second control unit 94 may cause the first light source unit 31 and one of the second light source unit 32 and the third light source unit 33 to emit visible light (red light+green light or red light+blue light). For example, when causing the first light source unit 31 and the third light source unit 33 to emit illumination light (red light+blue light) to the object, the image processing unit 91 preferably generates the background image and the fluorescence image by performing the processing similar to the processing for the G pixel as described above, for the B pixel as described above, and the processing similar to the processing for the B pixel as described above, for the G pixel.

Furthermore, in the first embodiment, the image processing unit 91 performs binarization for the background image, but may perform binarization for the fluorescence image, or may perform binarization for each of the background image and the fluorescence image. This makes it possible to emphasize the fluorescent area on the composite image. As a matter of course, the image processing unit 91 may omit the binarization for each of the background image and the fluorescence image. This makes it possible to simplify the process.

Furthermore, in the first embodiment, the image processing unit 91 performs colorization for the fluorescence image, but may perform colorization for the background image, or may perform colorization for the background image and the fluorescence image. In this case, the image processing unit 91 performs colorization for each of the background image and the fluorescence image so that the background image and the fluorescence image have different colors. This makes it possible to emphasize the fluorescent area on the composite image. As a matter of course, the image processing unit 91 may omit the colorization for each of the background image and the fluorescence image. This makes it possible to simplify the process.

Furthermore, in the first embodiment, the first light source unit 31, the second light source unit 32, and the fourth light source unit 34 are caused to emit light in the fluorescence observation mode, but, for example, a light source configured to be able to emit white light and a cut filter configured to block a blue wavelength band and transmit light in a wavelength band other than the blue wavelength band may be provided so that the cut filter is arranged on a white-light optical path through which white light is emitted, in the fluorescence observation mode. As a matter of course, the cut filter having a transmission characteristic of blocking a green wavelength band and transmitting light in a wavelength band other than the green wavelength band may be applied.

Furthermore, in the first embodiment, a cut filter configured to block one of the green and blue wavelength bands and transmit light in a wavelength band other than the green and blue wavelength bands may be employed, even if the cut filter is removably provided on the optical path between the optical system 211 and the cut filter 213 so as to be inserted in the optical path between the optical system 211 and the cut filter 213, in the fluorescence observation mode.

Modification of First Embodiment

Next, a modification of the first embodiment will be described. In the first embodiment described above, an image is captured by one image sensor 212 (single plate) having the Bayer array, but in the modification of the first embodiment, a plurality of image sensors is used.

Figure 14:
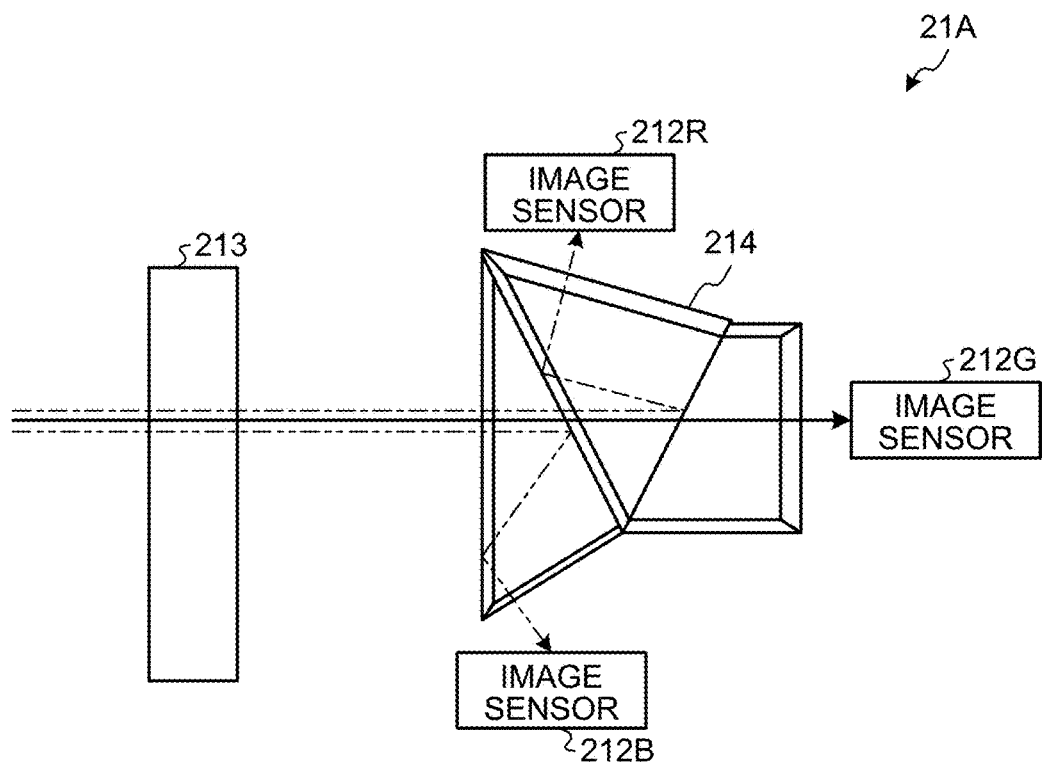
FIG. 14 is a conceptual diagram illustrating a configuration of an imaging unit according to a modification of the first embodiment.

FIG. 14 is a conceptual diagram illustrating a configuration of an imaging unit according to a modification of the first embodiment. The imaging unit 21A illustrated in FIG. 14 includes an image sensor 212R, an image sensor 212G, an image sensor 212B, and a dichroic prism 214, in place of the image sensor 212 described above.

The image sensor 212R includes the pixel portion 212a described above, receives red light split by the dichroic prism 214 which is described later, and performs photoelectric conversion to generate image data.

The image sensor 212G includes the pixel portion 212a described above, receives green light split by the dichroic prism 214 which is described later, and performs photoelectric conversion to generate image data.

The image sensor 212B includes the pixel portion 212a described above, receives blue light split by the dichroic prism 214 which is described later, and performs photoelectric conversion to generate image data.

The dichroic prism 214 emits red light and fluorescence, obtained from light incident thereon through the cut filter 213, to the image sensor 212R, emits green light and fluorescence to the image sensor 212G, and emits blue light and fluorescence to the image sensor 212B.

The medical observation system including the imaging unit 21A having such a configuration performs processing similar to that in the medical observation system 1 described above (see FIG. 6).

According to the modification of the first embodiment described above, the effects similar to those of the first embodiment described above may be obtained.

Second Embodiment

Next, a second embodiment will be described. In the first embodiment described above, the surgical microscope has been described as the medical observation system, but in the second embodiment, an endoscope system having a rigid endoscope will be described as the medical observation system. Note that the same configurations as those of the medical observation system 1 according to the first embodiment described above are denoted by the same reference signs, and detailed description thereof will be omitted.

Configuration of Medical Observation System

Figure 15:
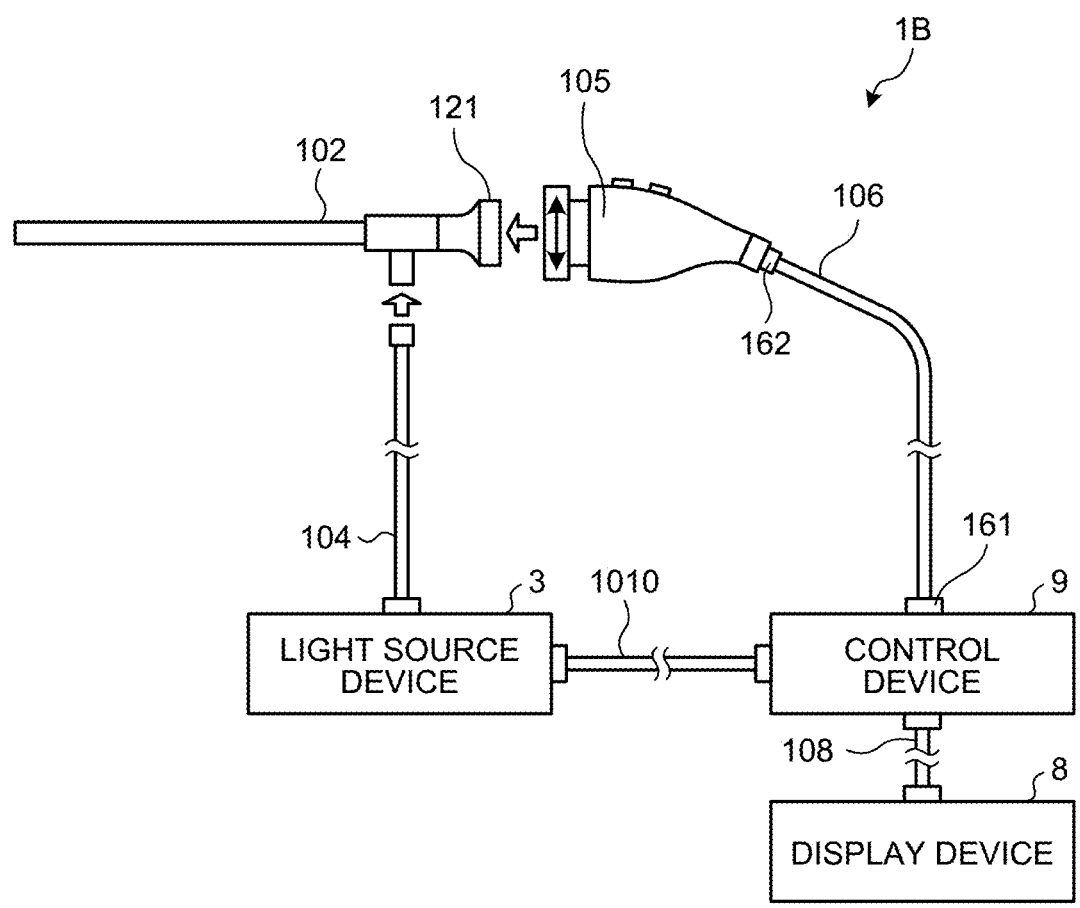
FIG. 15 is a diagram illustrating a schematic configuration of a medical observation system according to a second embodiment.

FIG. 15 is a diagram illustrating a schematic configuration of the medical observation system according to the second embodiment. A medical observation system 1B illustrated in FIG. 15 is used in the medical field and is a system configured to observe biological tissue in a subject such as a living body. Note that in the second embodiment, a rigid endoscope system using the rigid endoscope (insertion section 102) illustrated in FIG. 15 will be described as the medical observation system 1B.

The medical observation system 1B illustrated in FIG. includes the insertion section 102, a light source device 3, a light guide 104, an endoscope camera head 105 (endoscopic imaging device), a first transmission cable 106, a display device 8, a second transmission cable 108, a control device 9, and a third transmission cable 1010.

The insertion section 102 is rigid or at least partially flexible and has an elongated shape. The insertion section 102 is inserted into the subject such as a patient through a trocar. The insertion section 102 is internally provided with an optical system, such as a lens, configured to form an observation image.

The light guide 104 has one end that is detachably connected to the light source device 3 and the other end that is detachably connected to the insertion section 102. The light guide 104 guides illumination light supplied from the light source device 3 from the one end to the other end and supplies the illumination light to the insertion section 102.

The insertion section 102 includes an eyepiece 121 that is detachably connected to the endoscope camera head 105. Under the control by the control device 9, the endoscope camera head 105 receives light focused into an observation image by the insertion section 102, performs photoelectric conversion to generate image data (RAW data), and outputs the image data to the control device 9 via the first transmission cable 106.

The first transmission cable 106 has one end that is detachably connected to the control device 9 via a video connector 161, and the other end that is detachably connected to the endoscope camera head 105 via a camera head connector 162. The first transmission cable 106 transmits image data output from the endoscope camera head 105 to the control device 9 and transmits setting data, power, or the like output from the control device 9 to the endoscope camera head 105.

The second transmission cable 108 has one end that is detachably connected to the display device 8, and the other end that is detachably connected to the control device 9. The second transmission cable 108 transmits image data processed by the control device 9 to the display device 8.

The third transmission cable 1010 has one end that is detachably connected to the light source device 3, and the other end that is detachably connected to the control device 9. The third transmission cable 1010 transmits control data from the control device 9 to the light source device 3.

Functional Configuration of Main Portion of Medical Observation System

Figure 16:
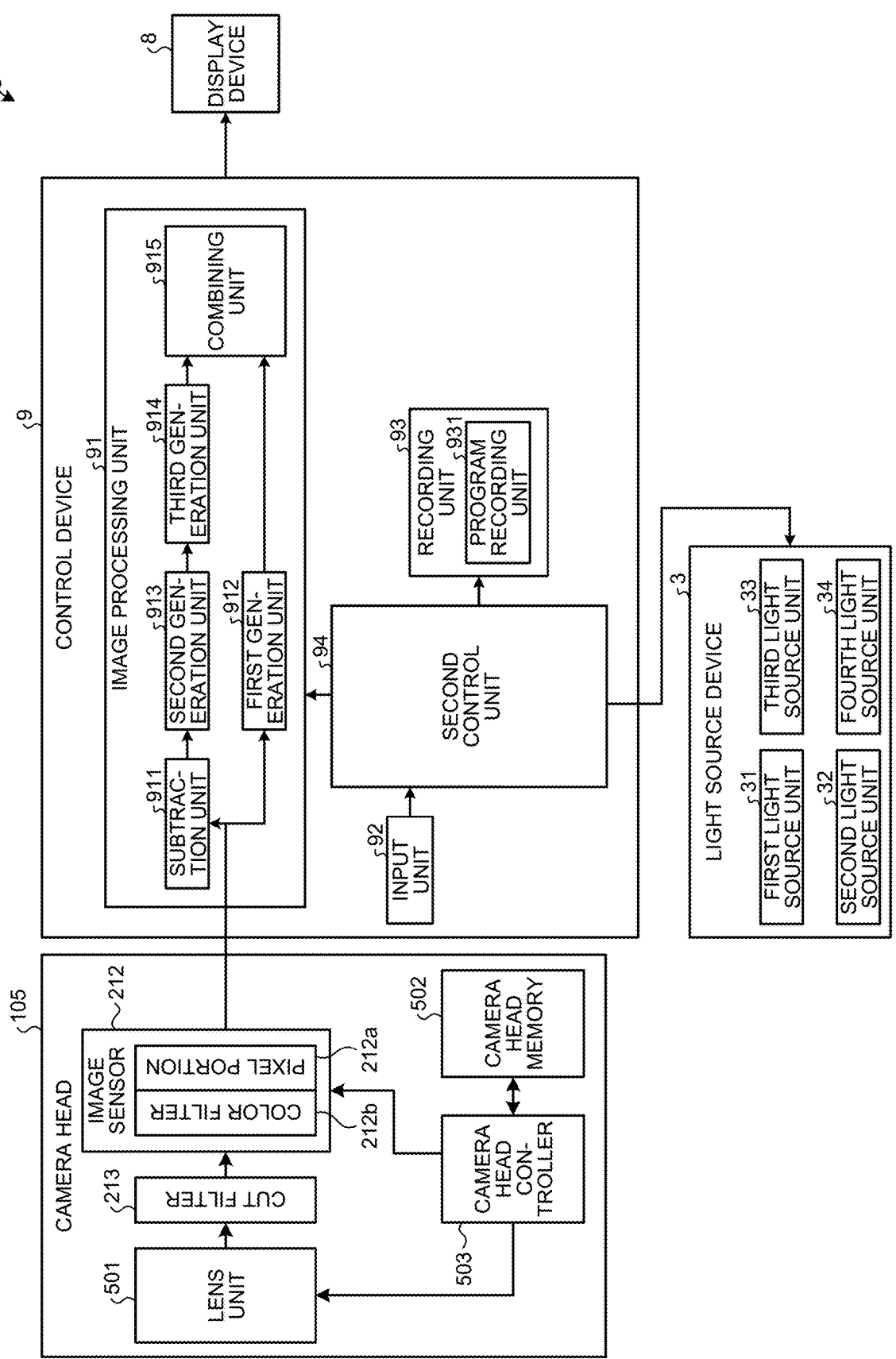
FIG. 16 is a block diagram illustrating a functional configuration of a main portion of the medical observation system according to the second embodiment.

Next, the functional configuration of a main portion of the medical observation system 1B described above will be described. FIG. 16 is a block diagram illustrating a functional configuration of the main portion of the medical observation system 1B.

Configuration of Endoscope Camera Head

First, a configuration of the endoscope camera head 105 will be described. The endoscope camera head 105 includes an image sensor 212, a cut filter 213, a lens unit 501, a camera head memory 502, and a camera head controller 503.

The lens unit 501 forms an image of an object focused by the optical system of the insertion section 102 on a light receiving surface of the image sensor 212. The focal position of the lens unit 501 is changeable. The lens unit 501 includes a plurality of lenses.

The camera head memory 502 records various information about the endoscope camera head 105 (e.g., pixel information about the image sensor 212, characteristics of the cut filter 213). Furthermore, the camera head memory 502 records various setting data and control parameters transmitted from the control device 9 via the first transmission cable 106. The camera head memory 502 includes a non-volatile memory or a volatile memory.

The camera head controller 503 controls the operation of each unit constituting the endoscope camera head 105 based on the setting data received from the control device 9 via the first transmission cable 106. The camera head controller 503 includes a timing generator (TG), a processor that is a processing device having hardware such as CPU, and a memory that is a temporary storage area used by the processor.

The medical observation system 1B having such a configuration performs processing similar to that in the medical observation system 1 described above (see FIG. 6).

According to the second embodiment described above, the effects similar to those of the first embodiment described above may be obtained, reducing the size of the endoscope camera head 105.

Third Embodiment

Next, a third embodiment will be described. In the third embodiment, a medical observation system that is applied to a flexible endoscope system using a flexible endoscope will be described. Note that the same configurations as those of the medical observation system 1 according to the first embodiment described above are denoted by the same reference signs, and detailed description thereof will be omitted.

Schematic Configuration of Medical Observation System

Figure 17:
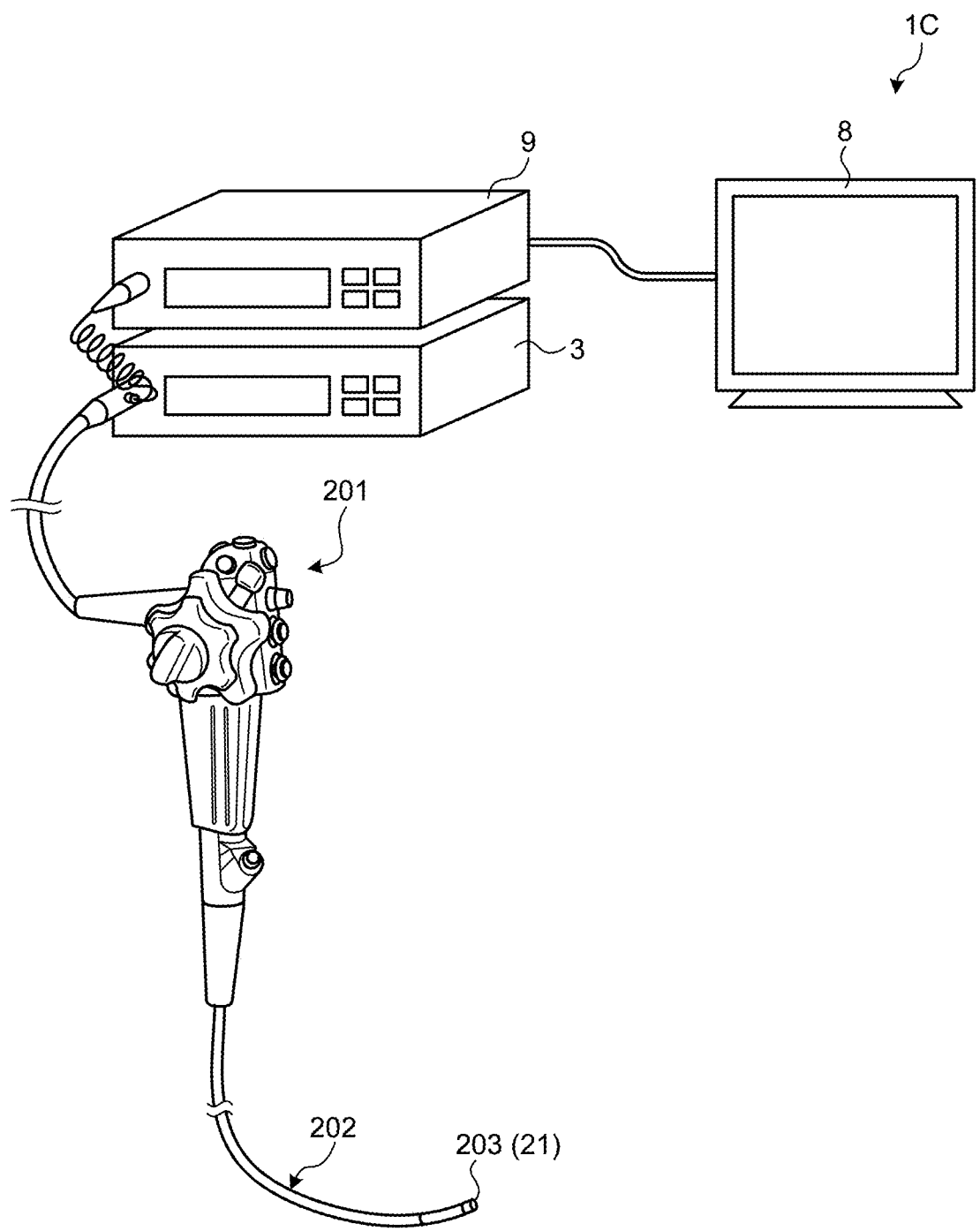
FIG. 17 is a diagram illustrating a schematic configuration of a medical observation system according to a third embodiment.

FIG. 17 is a diagram illustrating a schematic configuration of the medical observation system according to the third embodiment. A medical observation system 1C illustrated in FIG. 17 is configured to be inserted into a subject, image inside the subject to generate image data, and display an image based on the image data.

As illustrated in FIG. 17, the medical observation system 1C includes an endoscope 201 configured to capture an in-vivo image of an observed region by inserting an insertion section 202 into the subject to generate image data, a light source device 3, a display device 8, and a control device 9. The endoscope 201 is provided with an imaging unit 21 at a distal end portion 203 of the insertion section 202.

The medical observation system 1C having such a configuration performs processing similar to that in the medical observation system 1 described above (see FIG. 6).

According to the third embodiment described above, even the medical observation system 1C including the flexible endoscope 201 may obtain the effects similar to those of the first embodiment described above.

Other Embodiments

Various aspects of the disclosure may be formed by appropriately combining a plurality of component elements disclosed in the medical observation system according to the first to third embodiments of the present disclosure described above. For example, some component elements may be deleted from all the component elements described in the medical observation system according to the first to third embodiments of the present disclosure described above. Furthermore, the component elements described in the medical observation system according to the embodiments of the present disclosure described above may be appropriately combined.

Furthermore, in the medical observation system according to the first to third embodiments of the present disclosure, the word "unit" described above may be read as "means", "circuit", or the like. For example, the control unit may be read as control means or a control circuit.

Furthermore, a program executed by the medical observation system according to the first to third embodiments of the present disclosure is provided in the form of installable or executable file data and recorded in a computer-readable recording medium, such as a CD-ROM, flexible disk (FD), CD-R, digital versatile disk (DVD), USB medium, or flash memory.

Alternatively, a program executed by the medical observation system according to the first to third embodiments of the present disclosure may be configured to be stored on a computer connected to a network such as the Internet and provided by being downloaded via the network.

It is noted that, in the description of the flowchart herein, a context of processes between timings has been clearly shown by using expressions, such as "first", "then", and "subsequently", but the order of processes necessary to carry out the present disclosure is not uniquely defined by these expressions. In other words, the order of the processes in the flowchart described herein may be changed or modified within a consistent range. For example, the generation and colorization of the fluorescence image and the generation and binarization of the background image may be performed in parallel.

Some embodiments of the present application have been described in detail with reference to the drawings, but these are provided by way of examples, and it is possible to carry out the present disclosure in other forms, including the modes described in the present disclosure, to which various modifications and improvements may be made based on the knowledge of those skilled in the art.

Note that the present technique may also have the following configurations.

(Supplementary Note 1)

A medical image processing device including an image processing unit configured to perform image processing, based on image data generated by imaging reflected light of first visible light emitted to an object and fluorescence, by a medical imaging device, when a light source device simultaneously emits, to the object, the first visible light and excitation light that excites a fluorescent substance to emit the fluorescence, wherein the image processing unit is configured to generate an interpolation pixel value corresponding to a component of second visible light in a band different from a wavelength band of the first visible light, based on a first pixel value included in the image data and output from a pixel receiving the reflected light of the first visible light emitted to the object, generate a background image based on the first pixel value and the interpolation pixel value, and generate a fluorescence image based on a second pixel value included in the image data and output from a pixel receiving the fluorescence.

(Supplementary Note 2)

The medical image processing device according to Supplementary note 1, wherein the medical imaging device includes a cut filter provided near an incident surface of an image sensor and configured to block the excitation light but transmit the reflected light of the first visible light emitted to the object and the fluorescence.

(Supplementary Note 3)

The medical image processing device according to Supplementary note 1 or 2, wherein the image processing unit is configured to:

subtract the second pixel value from the first pixel value; and generate the background image, based on a result of the subtraction and the interpolation pixel value.

(Supplementary Note 4) The medical image processing device according to Supplementary note 1, wherein the medical imaging device includes an image sensor including a plurality of pixels, a first filter configured to transmit the first visible light and the fluorescence, and a second filter configured to transmit the second visible light and the fluorescence, the first filter and the second filter each being provided on a light receiving surface of each of the plurality of pixels, the image sensor is configured to image at least one of reflected light of at least one of the first visible light and the second visible light that are emitted to the object and the fluorescence, and generate image data, the first pixel value is output from a pixel on which the first filter is arranged, and the second pixel value is output from a pixel on which the second filter is arranged.

(Supplementary Note 5)

The medical image processing device according to Supplementary note 4, wherein the image processing unit is configured to:

divide a spectral sensitivity of a fluorescence wavelength of the first filter by a spectral sensitivity of a fluorescence wavelength of the second filter to obtain a divided value, multiply the divided value by the second pixel value to obtain a multiplication result, subtract the multiplication result from the first pixel value to obtain a subtraction result, and generate the background image based on the subtraction result and the interpolation pixel value.

(Supplementary Note 6)

The medical image processing device according to Supplementary note 4 or 5, wherein the first visible light is one of light in a red wavelength band and light in a green wavelength band, the first filter is one of a red filter configured to transmit the light in a red wavelength band and the fluorescence and a green filter configured to transmit the light in a green wavelength band and the fluorescence, and the second filter is a blue filter configured to transmit light in a blue wavelength band and the fluorescence.

(Supplementary Note 7)

The medical image processing device according to Supplementary note 6, wherein the light source device is configured to emit third visible light having a wavelength band different from the wavelength bands of the first visible light and the second visible light, the image sensor includes a third filter configured to transmit the third visible light and the fluorescence, the third visible light is another one of the light in a red wavelength band and the light in a green wavelength band, and the first filter is another one of the red filter configured to transmit the light in a red wavelength band and the fluorescence and the green filter configured to transmit the light in a green wavelength band and the fluorescence.

(Supplementary Note 8)

The medical image processing device according to Supplementary note 7, wherein the image processing unit is configured to generate the interpolation pixel value based on the first pixel value output from a pixel on which the green filter is arranged.

(Supplementary Note 9)

The medical image processing device according to Supplementary note 4 or 5, wherein the first visible light is one of light in a red wavelength band and light in a blue wavelength band, the first filter is one of a red filter configured to transmit the light in a red wavelength band and the fluorescence and a blue filter configured to transmit the light in a blue wavelength band and the fluorescence, and the second filter is a green filter configured to transmit light in a green wavelength band and the fluorescence.

(Supplementary Note 10)

The medical image processing device according to Supplementary note 9, wherein the light source device is configured to emit third visible light having a wavelength band different from the wavelength bands of the first visible light and the second visible light, the image sensor includes a third filter configured to transmit the third visible light and the fluorescence, the third visible light is another one of the light in a red wavelength band and the light in a blue wavelength band, and the first filter is another one of the red filter configured to transmit the light in a red wavelength band and the fluorescence and the blue filter configured to transmit the light in a blue wavelength band and the fluorescence.

(Supplementary Note 11)

The medical image processing device according to Supplementary note 10, wherein the image processing unit is configured to generate the interpolation pixel value based on the first pixel value output from a pixel on which the blue filter is arranged.

(Supplementary Note 12)

The medical image processing device according to any one of Supplementary notes 6 to 11, further including a control unit configured to control the light source device, the light source device includes:

a first light source unit configured to emit light in a red wavelength band;

a second light source unit configured to emit the light in a green wavelength band;

a third light source unit configured to emit the light in a blue wavelength band; and a fourth light source unit configured to emit the excitation light, wherein the control unit is configured to:

cause, in a white light observation mode for observation with white light, the first light source unit, the second light source unit, and the third light source unit to emit light, and cause, in a fluorescence observation mode for observation with the fluorescence, the first light source unit, the fourth light source unit, and one of the second light source unit and the third light source unit to emit light.

(Supplementary Note 13)

The medical image processing device according to any one of Supplementary notes 1 to 12, wherein the image processing unit is configured to generate a composite image obtained by combining the background image and the fluorescence image.

(Supplementary Note 14)

The medical image processing device according to any one of Supplementary notes 1 to 12, wherein the image processing unit is configured to perform binarization for at least one of the background image and the fluorescence image.

(Supplementary Note 15)

The medical image processing device according to any one of Supplementary notes 1 to 12, wherein the image processing unit is configured to perform colorization for at least one of the background image and the fluorescence image.

(Supplementary Note 16)

The medical image processing device according to any one of Supplementary notes 1 to 15, wherein
the fluorescent substance employs indocyanine green, and the excitation light has a center wavelength of 740 nm.

(Supplementary Note 17)

A medical image processing device including
an image processing unit configured to perform image processing, based on image data generated by imaging reflected light of first visible light emitted to an object and fluorescence, by a medical imaging device, when a light source device simultaneously emits, to the object, the first visible light and excitation light that excites a fluorescent substance to emit the fluorescence,
wherein the medical imaging device includes
a dichroic prism configured to split the reflected light and the fluorescence into a plurality of wavelength bands, and
a plurality of image sensors configured to receive light split into the plurality of wavelength bands by the dichroic prism and generate a plurality of pieces of the image data, and
the image processing unit is configured to:
generate an interpolation pixel value that interpolates a pixel value corresponding to a component of second visible light in a band different from a wavelength band of the first visible light, based on the image data;
generate a background image, based on the image data and the interpolation pixel value; and
generate a fluorescence image, based on the image data.

(Supplementary Note 18)

A medical observation system including:
the medical image processing device according to any one of Supplementary notes 1 to 17;
a support unit configured to rotatably support the medical imaging device; and
a base portion configured to rotatably hold a base end portion of the support unit and to be movable on a floor surface.

(Supplementary Note 19)

A medical observation system including:
the medical image processing device according to any one of Supplementary notes 1 to 17; and
an insertion section configured to be insertable into a subject and including an optical system configured to focus the reflected light and the fluorescence to form an image of an object on a light receiving surface of an image sensor.

(Supplementary Note 20)

The medical observation system according to Supplementary note 19, wherein
the insertion section is configured to be removable from the medical imaging device.

(Supplementary Note 21)

A method of processing an image executed by a medical image processing device configured to perform image processing, based on image data generated by imaging reflected light of first visible light emitted to an object and fluorescence, by a medical imaging device, when a light source device simultaneously emits, to the object, the first visible light and excitation light that excites a fluorescent substance to emit the fluorescence, the method including:
generating an interpolation pixel value corresponding to a component of second visible light in a band different from a wavelength band of the first visible light, based on a first pixel value included in the image data and output from a pixel receiving the reflected light of the first visible light emitted to the object;
generating a background image based on the first pixel value and the interpolation pixel value; and
generating a fluorescence image based on a second pixel value included in the image data and output from a pixel receiving the fluorescence.

According to the present disclosure, the size of the device may be effectively reduced.

Although the disclosure has been described with respect to specific embodiments for a complete and clear disclosure, the appended claims are not to be thus limited but are to be construed as embodying all modifications and alternative constructions that may occur to one skilled in the art that fairly fall within the basic teaching herein set forth.

What is claimed is:

1. A medical image processing device comprising:
image processing circuitry configured to perform image processing, based on image data generated by a medical imaging device that images first visible light reflected from an object and fluorescence emitted from a fluorescent substance of the object, under a condition a light source device simultaneously emits, to the object, the first visible light and excitation light that excites the fluorescent substance of the object to emit the fluorescence, wherein
the image processing circuitry is further configured to
generate an interpolation pixel value corresponding to a component of second visible light in a wavelength band different from a wavelength band of the first visible light, based on a first pixel value included in the image data and output from a pixel receiving the first visible light reflected from the object;
generate a background image based on the first pixel value and the interpolation pixel value; and
generate a fluorescence image based on a second pixel value included in the image data and output from a pixel receiving the fluorescence, wherein the medical imaging device includes an image sensor including
a plurality of pixels;
a first filter configured to transmit the first visible light and the fluorescence; and
a second filter configured to transmit the second visible light and the fluorescence, the first filter and the second filter each being provided on a light receiving surface of each corresponding one of the plurality of pixels, wherein the image sensor is configured to
image at least one of the fluorescence and at least one of the first visible light and the second visible light that are reflected from the object; and
generate image data,
the first pixel value being output from a pixel on which the first filter is arranged and the second pixel value being output from a pixel on which the second filter is arranged.

2. The medical image processing device according to claim 1, wherein the medical imaging device further includes a cut filter provided near an incident surface of the image sensor and configured to block the excitation light but transmit the first visible light reflected from the object and the fluorescence emitted from the fluorescent substance of the object.

3. The medical image processing device according to claim 1, wherein the image processing circuitry is further configured to
subtract the second pixel value from the first pixel value; and
generate the background image, based on a result of the subtraction and the interpolation pixel value.

4. The medical image processing device according to claim 1, wherein the image processing circuitry is further configured to
divide a spectral sensitivity of a fluorescence wavelength of the first filter by a spectral sensitivity of a fluorescence wavelength of the second filter to obtain a divided value;
multiply the divided value by the second pixel value to obtain a multiplication result;
subtract the multiplication result from the first pixel value to obtain a subtraction result; and
generate the background image based on the subtraction result and the interpolation pixel value.

5. The medical image processing device according to claim 1, wherein
the first visible light is one of light in a red wavelength band and light in a green wavelength band,
the first filter is one of a red filter configured to transmit the light in a red wavelength band and the fluorescence and a green filter configured to transmit the light in a green wavelength band and the fluorescence, and
the second filter is a blue filter configured to transmit light in a blue wavelength band and the fluorescence.

6. The medical image processing device according to claim 5, wherein
the light source device is configured to emit third visible light having a wavelength band different from the wavelength bands of the first visible light and the second visible light,
the image sensor includes a third filter configured to transmit the third visible light and the fluorescence,
the third visible light is the other of the light in a red wavelength band and the light in a green wavelength band, and
the third filter is the other of the red filter and the green filter.

7. The medical image processing device according to claim 6, wherein the image processing circuitry is further configured to generate the interpolation pixel value based on the first pixel value output from a pixel on which the green filter is arranged.

8. The medical image processing device according to claim 5, further comprising:
control circuitry configured to control the light source device, wherein
the light source device includes
a first light source configured to emit the light in a red wavelength band;
a second light source configured to emit the light in a green wavelength band;
a third light source configured to emit the light in a blue wavelength band; and
a fourth light source configured to emit the excitation light,
wherein the control circuitry is further configured to
cause, in a white light observation mode for observation with white light, the first light source, the second light source, and the third light source to emit light, and
cause, in a fluorescence observation mode for observation with the fluorescence, the first light source, the fourth light source, and one of the second light source and the third light source to emit light.

9. The medical image processing device according to claim 1, wherein
the first visible light is one of light in a red wavelength band and light in a blue wavelength band,
the first filter is one of a red filter configured to transmit the light in a red wavelength band and the fluorescence and a blue filter configured to transmit the light in a blue wavelength band and the fluorescence, and
the second filter is a green filter configured to transmit light in a green wavelength band and the fluorescence.

10. The medical age processing device according to claim 9, wherein
the light source device is configured to emit third visible light having a wavelength band different from the wavelength bands of the first visible light and the second visible light,
the image sensor includes a third filter configured to transmit the third visible light and the fluorescence,
the third visible light is the other of the light in a red wavelength band and the light in a blue wavelength band, and
the third filter is the other of the red filter and the blue filter.

11. The medical image processing device according to claim 10, wherein the image processing circuitry is configured to generate the interpolation pixel value based on the first pixel value output from a pixel on which the blue filter is arranged.

12. The medical image processing device according to claim 1, wherein the image processing circuitry is further configured to generate a composite image obtained by combining the background image and the fluorescence image.

13. The medical image processing device according to claim 1, wherein the image processing circuitry is further configured to perform binarization for at least one of the background image and the fluorescence image.

14. The medical image processing device according to claim 1, wherein the image processing circuitry is further configured to perform colorization for at least one of the background image and the fluorescence image.

15. The medical image processing device according to claim 1, wherein
the fluorescent substance employs indocyanine green, and
the excitation light has a center wavelength of 740 nm.

16. A medical observation system comprising:
the medical image processing device according to claim 1;
a support structure configured to rotatably support the medical imaging device; and
a base structure configured to rotatably hold a base end portion of the support structure and to be movable on a floor surface.

17. A medical observation system comprising:
the medical image processing device according to claim 1; and
an insertion section configured to be insertable into a subject and including an optical system configured to focus the first visible light reflected from the object and the fluorescence emitted from the fluorescent substance of the object, and to form an image of the object on the light receiving surface of the image sensor.

18. A method of processing an image executed by a medical image processing device, the method comprising:
performing image processing, based on image data generated by a medical imaging device that images first visible light reflected from an object and fluorescence emitted from a fluorescent substance of the object, under a condition a light source device simultaneously emits, to the object, the first visible light and excitation light that excites the fluorescent substance of the object to emit the fluorescence;

generating an interpolation pixel value corresponding to a component of second visible light in a wavelength band different from a wavelength band of the first visible light, based on a first pixel value included in the image data and output from a pixel receiving the first visible light reflected from the object;

generating a background image based on the first pixel value and the interpolation pixel value; and generating a fluorescence image based on a second pixel value included in the image data and output from a pixel receiving the fluorescence, wherein the medical imaging device includes an image sensor including a plurality of pixels;

a first filter configured to transmit the first visible light and the fluorescence; and a second filter configured to transmit the second visible light and the fluorescence, the first filter and the second filter each being provided on a light receiving surface of each corresponding one of the plurality of pixels, wherein the image sensor is configured to image at least one of the fluorescence and at least one of the first visible light and the second visible light that are reflected from the object; and generate image data, the first pixel value being output from a pixel on which the first filter is arranged, and the second pixel value being output from a pixel on which the second filter is arranged.

* * * * *